(12) United States Patent
Zhang

(10) Patent No.: US 8,558,069 B2
(45) Date of Patent: Oct. 15, 2013

(54) **INBRED *CUCURBITA PEPO* PUMPKIN HSPMR7B1 HAVING A MUTANT ALLELE FOR POWDERY MILDEW RESISTANCE**

(75) Inventor: Qi Zhang, Rocky Ford, CO (US)

(73) Assignee: Hollar Seeds, Rocky Ford, CO (US)

( * ) Notice: Subject to any disclaimer, the term of this patent is extended or adjusted under 35 U.S.C. 154(b) by 324 days.

(21) Appl. No.: 12/878,220

(22) Filed: Sep. 9, 2010

(65) Prior Publication Data

US 2011/0004954 A1 Jan. 6, 2011

Related U.S. Application Data

(63) Continuation-in-part of application No. 11/678,724, filed on Feb. 26, 2007, now abandoned.

(51) Int. Cl.
| | | |
|---|---|---|
| *A01H 5/00* | (2006.01) | |
| *A01H 5/10* | (2006.01) | |
| *A01H 1/00* | (2006.01) | |
| *C12N 5/04* | (2006.01) | |
| *C12N 15/82* | (2006.01) | |

(52) U.S. Cl.
USPC ........... 800/310; 435/410; 800/260; 800/278; 800/300; 800/279; 800/302; 800/301

(58) Field of Classification Search
None
See application file for complete search history.

(56) References Cited

U.S. PATENT DOCUMENTS

| 5,523,520 A | 6/1996 | Hunsperger et al. |
| 6,916,974 B2 * | 7/2005 | Superak et al. ............... 800/310 |
| 7,166,772 B2 * | 1/2007 | Superak ........................ 800/310 |

OTHER PUBLICATIONS

Ahmed et al (1998, Sudan J. Agri. Res. 1:57-60).*
McGrath et al (2006, Powdery Mildew Resistant Pumpkin Cultivar Evaluation, New York 2006 IN: Midwest Vegetable Variety Trial Report for 2006. Compiled by Elizabeth T. Maynard and Christopher C. Gunter. Bulletin No. B18048. Dept. of Horticulture and Landscape Architecture, Office of Agricultural Research Programs, Purdue University, W. Lafayette, I.*
U.S. Appl. No. 11/678,724, filed Aug. 28, 2008, Zhang, Qi.
U.S. Appl. No. 11/678,724, filed Aug. 28, 2008, Zhang, Qi, Office Action dated Oct. 8, 2009.
U.S. Appl. No. 11/678,724, filed Aug. 28, 2008, Zhang, Qi, Response to Office Action of Oct. 8, 2009 dated Feb. 8, 2010.
U.S. Appl. No. 11/678,724, filed Aug. 28, 2008, Zhang, Qi, Final Office Action dated May 18, 2010.
Eshed, et al., 1996. Less-than-additive epistatic interactions of quantitative trait loci in tomato. Genetics. 143:1807-1817.
Kraft, et al., 2000. Linkage disequilibrium and fingerprinting in sugar beet. Theor. Appl. Genet. 101:323-326.
Contin, 1978. Interspecific transfer of powdery mildew resistance in the genus *Curcurbita*, Ph.D. Thesis, Cornell University.
Ahmed, et al., 1998. Sudan J. Agri. Res. 1:57-60.

* cited by examiner

*Primary Examiner* — Anne Kubelik
(74) *Attorney, Agent, or Firm* — Jondle Plant Sciences Division of Swanson & Bratschun, L.L.C.

(57) ABSTRACT

The present invention relates to a plant, seed, variety and hybrid of the inbred *Cucurbita pepo* pumpkin line HSPMR7B1, which has a mutant allele designated Pm2 which results in a powdery mildew resistant plant. The invention also relates to crossing inbreds, varieties and hybrids containing the Pm2 mutant allele to produce powdery mildew resistant *C. pepo* plants.

18 Claims, No Drawings

INBRED *CUCURBITA PEPO* PUMPKIN HSPMR7B1 HAVING A MUTANT ALLELE FOR POWDERY MILDEW RESISTANCE

CROSS-REFERENCE TO RELATED APPLICATIONS

This application is a Continuation-In-Part of and claims priority under 35 U.S.C. §119 from U.S. application Ser. No. 11/678,724, filed Feb. 26, 2007, which is incorporated herein in their entirety by reference.

BACKGROUND OF THE INVENTION

The present invention relates to a new pumpkin inbred line (*Cucurbita pepo* L.), designated HSPMR7B1, which has a novel mutant powdery mildew resistant (PMR) allele (Pm2) conferring to *Cucurbita pepo* plants a strong powdery mildew resistance. The present invention also relates to plants and seeds of the family or line carrying the PMR allele in the homozygous and heterozygous states. In addition, another aspect of the present invention is directed to transferring the PMR allele to plants in the same species lacking the allele, and is useful for producing novel types and varieties of powdery mildew resistant *Cucurbita pepo*. All publications cited in this application are herein incorporated by reference.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possesses the traits to meet the program goals. The goal is to combine in a single variety an improved combination of desirable traits from the parental germplasm. These important traits may include higher seed yield, resistance to diseases and insects, better stems and roots, tolerance to drought and heat, and better agronomic quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable plant. This approach has been used extensively for breeding disease-resistant plants. Various recurrent selection techniques are used to improve quantitatively inherited traits controlled by numerous genes. The use of recurrent selection in self-pollinating crops depends on the ease of pollination, the frequency of successful hybrids from each pollination and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars; those still deficient in a few traits may be used as parents to produce new populations for further selection.

These processes, which lead to the final step of marketing and distribution, usually take from eight to twelve years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of pumpkin and squash plant breeding is to develop new, unique and superior pumpkin and squash cultivars and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same pumpkin and squash traits.

Each year, the plant breeder selects the germplasm to advance to the next generation. This germplasm is grown under unique and different geographical, climatic and soil conditions, and further selections are then made during and at the end of the growing season. The cultivars that are developed are unpredictable because the breeder's selection occurs in unique environments with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same cultivar twice by using the same original parents and the same selection techniques. This unpredictability results in the expenditure of large amounts of research monies to develop superior new pumpkin and squash cultivars.

The development of new pumpkin and squash lines requires the development and selection of pumpkin and squash varieties, the crossing of these varieties and selection of superior hybrid crosses. The hybrid seed is produced by manual crosses between selected male-fertile parents or by using male sterility systems. These hybrids are selected for certain single gene traits such as fruit color, flower color, pubescence color or herbicide resistance which indicate that the seed is truly a hybrid. Additional data on parental lines, as well as the phenotype of the hybrid, influence the breeder's decision whether to continue with the specific hybrid cross.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Pedigree breeding is used commonly for the improvement of self- and cross-pollinating crops. Two parents that possess favorable, complementary traits are crossed to produce an $F_1$.

An $F_2$ population is produced by selfing one or several $F_1$s. Selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as the parents of commercial hybrids or new cultivars.

Mass and recurrent selections can be used to improve populations of either self- or cross-pollinating crops. A genetically variable population of heterozygous individuals is either identified, or created, by intercrossing several different parents or intra-crossing in a heterogeneous population. The best plants are selected based on individual superiority, outstanding progeny, or excellent combining ability. The selected plants are intra-crossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, pumpkin and squash breeders commonly harvest two or more seeds from the fruit of each plant in a population and bulk them to form a bulk sample. Part of the bulk is used to plant the next generation and part is put in reserve. The procedure has been referred to as modified single-seed descent or the "pod-bulk" (for bean crops) technique.

The multiple-seed procedure has been used to save labor at harvest. It is considerably faster to extract seeds with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

Isozyme Electrophoresis and RFLPs have been widely used to determine genetic composition. Shoemaker and Olsen, (Molecular Linkage Map of Soybean (*Glycine max* L. Merr.) p 6.131-6.138 in S. J. O'Brien (ed) *Genetic Maps: Locus Maps of Complex Genomes*, Cold Spring Harbor Laboratory Press, Cold Spring Harbor, N.Y., (1993)) developed a molecular genetic linkage map that consisted of 25 linkage groups with about 365 RFLP, 11 RAPD, three classical markers and four isozyme loci. See also, Shoemaker, R. C., RFLP Map of Soybean, p 299-309, in Phillips, R. L. and Vasil, I. K., Eds. *DNA-Based Markers in Plants*, Kluwer Academic Press, Dordrecht, the Netherlands (1994).

SSR technology is currently the most efficient and practical marker technology; more marker loci can be routinely used and more alleles per marker locus can be found using SSRs in comparison to RFLPs. For example, Diwan and Cregan described a highly polymorphic microsatellite locus in soybean with as many as 26 alleles. (Diwan, N. and Cregan, P. B., *Theor. Appl. Genet.* 95:22-225, 1997.) SNPs may also be used to identify the unique genetic composition of the invention and progeny varieties retaining that unique genetic composition. Various molecular marker techniques may be used in combination to enhance overall resolution.

Molecular markers, which includes markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding is another method of introducing new traits into pumpkin and squash varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogues like 5-bromouracil), antibiotics, alkylating agents (such as sulfur mustards, nitrogen mustards, epoxides, ethylene amines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in *Principles of Cultivar Development* by Fehr, Macmillan Publishing Company, 1993.

The production of double haploids can also be used for the development of homozygous varieties in a breeding program. Double haploids are produced by the doubling of a set of chromosomes from a heterozygous plant to produce a completely homozygous individual. For example, see Wan et al., *Theor. Appl. Genet.*, 77:889-892, 1989.

Descriptions of other breeding methods that are commonly used for different traits and crops can be found in one of several reference books (e.g., Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

The genus *Cucurbita* is composed of five species: *C. pepo, C. maxima, C. moschta, C. mixta* and *C. ficifolia*. The terms "pumpkin", "squash" and "gourd" cannot be directly related to the species; forms of several are called pumpkins and the same is true of squashes and gourds. The term "pumpkin" is normally applied to the edible fruit of any species of *Cucurbita* utilized when ripe as a table vegetable, in pies, or as an ornamental. The term "squash" was evidently derived from a north-eastern American Indian word indicating a fruit, apparently *Cucurbita pepo* L., eaten raw as an immature fruit or consumed for the mature seed (T. W. Whitaker 1986. Breeding Vegetable Crops, pp. 210-223). It is now also applied to certain baking cultivars of *C. pepo* (e.g., Acorn), *C. moschta* (e.g., butternut), *C. mixma* (e.g., Orange Banana) and *C. mixta* (e.g., Cushaw) that are used in the mature state. The terms "pumpkin", "squash" and "gourd" are confined to the species *C. pepo. Pepo* is an extremely large and diverse species in the genus *Cucurbita* which is separated into four categories: Halloween pumpkin, summer squash, winter squash and ornamental gourd. Each category is composed of many cultural types and has many varieties over the world. The *pepo* crops are widely cultivated and play a significant role in human nutrition and economic development globally.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools and methods which are meant to be exemplary, not limiting in scope. In various embodiments, one or more of the above-described problems have been reduced or eliminated, while other embodiments are directed to other improvements.

According to the invention, there is provided a novel pumpkin inbred line designated HSPMR7B1. This invention thus relates to a *C. pepo* seed, a *C. pepo* plant, a *C. pepo* variety and a *C. pepo* hybrid, which are derived from HSPMR7B1, and to a method for producing a *C. pepo* plant. More specifically, the invention relates to a pumpkin inbred line designated HSPMR7B1 which has a genuine powdery mildew resistance.

Another aspect of the invention relates to any *C. pepo* seed or plant having the mutant allele Pm2 which is generated from HSPMR7B1 or to any *C. pepo* seed or plant having the mutant allele Pm2 which is derived from an open pollinated plant, cross or hybrid of HSPMR7B1.

In another aspect, the present invention provides regenerable cells for use in tissue culture. The tissue culture will preferably be capable of regenerating plants having the physiological and morphological characteristics of the foregoing *C. pepo* plant, and of regenerating plants having substantially the same genotype as the foregoing *C. pepo* plant. Preferably, the regenerable cells in such tissue cultures will be embryos, protoplasts, meristematic cells, callus, pollen, leaves, anthers, pistils, stems, petioles, roots, root tips, fruits, seeds, flowers, cotyledons, hypocotyls or the like. Still further, the present invention provides *C. pepo* plants regenerated from the tissue cultures of the invention.

Another aspect of the invention is to provide methods for producing other *C. pepo* plants derived from HSPMR7B1 plant having the PMR allele Pm2. *C. pepo* lines derived by the use of those methods are also part of the invention.

The invention also relates to methods for producing a *C. pepo* plant containing in its genetic material one or more transgenes and to the transgenic *C. pepo* plant produced by that method.

The invention further provides methods for developing *C. pepo* plants in a *C. pepo* plant breeding program using plant breeding techniques including recurrent selection, backcrossing, pedigree breeding, restriction fragment length polymorphism enhanced selection, genetic marker enhanced selection and transformation. *C. pepo* seeds, plants and parts thereof produced by such breeding methods are also part of the invention.

The invention further provides for a *C. pepo* plant having consistent increased resistance over the growing season to powdery mildew and exhibiting a mean colony count of powdery mildew, wherein said increased resistance is exhibiting at least about 75%, 73%, 72%, 65%, 60%, 59%, 58%, 55%, 53%, 50%, 47%, 45%, 42%, 38%, 36%, 33%, 31%, 29%, 28%, 27% and 25% less mean powdery mildew colony counts per plant when compared to commercial pumpkin varieties in an environment having a level of powdery mildew present.

In addition to the exemplary aspects and embodiments described above, further aspects and embodiments will become apparent by study of the following descriptions.

DEFINITIONS

In the description and tables that follow, a number of terms are used. In order to provide a clear and consistent understanding of the specification and claims, including the scope to be given such terms, the following definitions are provided:

Allele. An "allele" is any of one or more alternative form of a gene, all of which relate to one trait or characteristic. In a diploid cell or organism, the two alleles of a given gene occupy corresponding loci on a pair of homologous chromosomes.

Mean colonies per square inch. As used herein, "mean colonies per square inch" means the mean count of the number of powdery mildew colonies on a square inch of plant parts, including the leaf, petiole and stems. The fungal colonies are formed by conidia.

Backcross. "Backcross" is a breeding method in which a breeder repeatedly crosses hybrid progeny back to one of the parents, for example, a first generation hybrid $F_1$ with one of the parents of the $F_1$ hybrid.

Commercial pumpkin. "Commercial pumpkin" means a pumpkin (*C. pepo*) that has been commercially sold. A commercial pumpkin is a pumpkin plant that does not contain the PMR allele Pm2.

Complete growing season. "Complete growing season" means from the *C. pepo* planting date until the date that 95% of *C. pepo* leaves have died naturally and not due to disease.

Consistent resistance. "Consistent resistance" refers to plants expressing resistance to powdery mildew for the complete growing season when powdery mildew is present in the environment.

Essentially all the physiological and morphological characteristics. A plant having "essentially all the physiological and morphological characteristics" means a plant having the physiological and morphological characteristics, except for the characteristics derived from the converted gene.

Gene converted (conversion). "Gene converted" or "Single gene converted" (or conversion) plant refers to plants which are developed by a plant breeding technique called backcrossing wherein essentially all of the desired morphological and physiological characteristics of an inbred are recovered in addition to the one or more genes transferred into the inbred via the backcrossing technique or via genetic engineering.

Pm2. "Pm2" refers to the mutant allele of the powdery mildew resistant gene in HSPMR7B1 of the present invention deposited a sample under ATCC Accession Number PTA-8167, which confers a stronger powdery mildew resistance to *C. pepo* plants than the existing allele Pm in the common commercial *C. pepo* varieties.

Increased resistance. "Increased resistance" means improved resistance to powdery mildew caused by *Sphaerotheca fuliginea* Poll. and/or *Erysiphe cichoracearum* DC when compared to/versus commercial pumpkin varieties. That is, the plant's resistance can be highly resistant to powdery mildew (i.e., have few or no colony counts of powdery mildew on any plant parts) or increased resistance (i.e., when compared to/versus commercial pumpkin varieties, the varieties of the present invention which contain the PMR mutant allele have a lower colony counts of powdery mildew on their plant parts than the plant parts of the commercial pumpkin varieties). The increased resistance reflects the capability of a plant to reduce the establishment of an infection and may for example, be calculated by determining the success of the plant surviving upon contact with the infectious agent (i.e., the powdery mildew fungus). Increased resistance is also intended to mean that the disease symptoms caused by powdery mildew are minimized or lessened.

Leaf. "Leaf" means an above-ground plant organ specialized for photosynthesis and transpiration. For these purposes, a leaf is typically flat (laminar) and thin, to expose the cells containing chloroplast to light over a broad area, and to allow light to penetrate fully into the tissues and to allow heat to diffuse optimally.

Pedigree breeding/selection. "Pedigree breeding" is a breeding method used during the inbreeding of populations of self- and cross-pollinated species for the development of desirable homogeneous lines. Pedigree selection generally begins with an $F_2$ population and continues until homogeneous lines are developed.

Petiole. "Petiole" means the stalk of a leaf, attaching the leaf blade to the stem.

Plant. "Plant" includes plant cells, plant protoplasts, plant cells of tissue culture from which *C. pepo* plants can be regenerated, plant calli, plant clumps and plant cells that are intact in plants, or parts of plants such as pollen, flowers, seeds, leaves, stems, rind, flesh and the like.

PMR. "PMR" refers to a *C. pepo* plant phenotypically displaying a level of powdery mildew resistance. The level of powdery mildew on plants is divided into six PMR scores or categories consisting of 0, 1, 2, 3, 4, 5, in which 0 indicates that the plants are completely resistant to the disease and there are no symptoms of the disease on the plants at all, and a rating of 5 indicates that the plants are 100% infected and susceptible.

PMS. "PMS" refers to a *C. pepo* plant phenotypically displaying powdery mildew susceptibility.

Quantitative Trait Loci (QTL). "Quantitative trait loci (QTL)" refer to genetic loci that control to some degree numerically representable traits that are usually continuously distributed.

Regeneration. "Regeneration" refers to the development of a plant from tissue culture.

Stem. "Stem" means the above ground structures that have vascular tissue and that support, for example, leaves, flowers, seed, fruit, etc. The stem is normally divided into nodes and internodes, the nodes hold buds which grow into for example, one or more leaves, inflorescence (flowers), cones or other stems (or branches), while the internodes act as spaces that distance one node from another.

Yield. "Yield" means the total weight in kilograms of marketable harvested fruit from an experimental plot or field.

DETAILED DESCRIPTION OF THE INVENTION

The present invention relates to an inbred pumpkin designated HSPMR7B1 (*C. pepo*) with a novel PMR mutant allele (Pm2), showing strong powdery mildew resistance on the pumpkin plants. As used herein powdery mildew resistance refers to pumpkin plants that display little to no powdery mildew symptoms throughout the growing season.

According to the invention, there is provided the pumpkin inbred HSPMR7B1 carrying a novel PMR mutant allele designated Pm2. This invention thus relates to a *C. pepo* seed, a *C. pepo* plant, a *C. pepo* variety, a *C. pepo* hybrid, and to a method for producing a *C. pepo* plant which derived from H7B11 through a direct or indirect way of genetic recombination. More specifically, the invention relates to a pumpkin line having a PMR mutant allele designated Pm2 which produces a *C. pepo* plant with strong powdery mildew resistance.

Another aspect of the invention relates to any *C. pepo* seed or plant having the mutant allele Pm2.

A common disease of *C. pepo* crops is powdery mildew which is largely caused by two different fungi: *Sphaerotheca fuliginea* Poll. and *Erysiphe cichoracearum* DC. Powdery mildew epidemics are ubiquitous and often result in considerable losses to fields of pumpkin, squash and gourd. Powdery mildew infections on the crops appear as a white powdery growth that develops on the leaf blades, peduncles, and stems of susceptible plants. Usually infection begins on older leaves and then spreads to other parts of the plant. It frequently compromises yield by reducing the leaf area available for photosynthesis, accelerating senescence, and, ultimately, killing the infected plants. Therefore, the disease is one of the main limiting factors of pumpkin, squash and gourd production around the world.

To solve the powdery mildew disease problem, breeding for powdery mildew resistance has been conducted worldwide for a number of years. There is an existing powdery mildew resistant gene (Pm) in *Cucurbita pepo* that was derived from an interspecific breeding process which was conducted by Cornell University researchers, including Dr. Maximo E. Contin in the time period of 1970s-1990s. After the gene was transferred to *C. pepo* from two wild *Cucurbita* species, *C. ecuadorensis* and *C. martinezii*, some *C. pepo* lines with PMR were developed by the end of 1990s. The moment the PMR lines were released, all of the seed companies in America started to integrate the Pm allele into their *C. pepo* materials; which include the *C. pepo* summer squash, winter squash and pumpkins. All powdery mildew resistant *C. pepo* varieties developed recently contain this allele, which includes the pumpkin varieties discussed in our patent application such as Merlin, Magic Lantern and Spartan. It was reported that the transferred powdery resistance to *C. pepo* was governed by a single dominant gene with additional modifier genes influencing the level of resistance. Resistance in crosses involving *C. pepo* and *C. martinezii* was dominant at the seedling stage, and incompletely dominant at maturity. The inheritance of resistance at the seedling stage and at maturity could be explained by the action of a major dominant gene, but the phenotypic expression of resistance at maturity appeared to be under the influences of other genes and/or possible environmental factors (M. E. Contin. 1978). It was also concluded that the most common commercially available pumpkin and squash varieties had powdery mildew resistance which is conferred by a single co-dominant gene (M. T. Megrath. 2004). Both cases mentioned above indicated that the phenotypic expression of the Pm gene in *C. pepo* plants was mainly in an incompletely dominant manner even though it acts like a single dominant gene at the seedling stage. The alleles compared with Pm2 in the application are the existing Pm and a recessive allele pm. The most common commercially available pumpkin and squash varieties have powdery mildew resistance which is conferred by a single co-dominant gene (See M. T. Mcgrath. 2004. Managing powdery mildew in winter squash with genetic control and chemical control. *Plant Pathology*, Cornell Univ. Pub. No. P-2004-0016-Nea; and R. Cohen et. al. 2004. Single-gene resistance to powdery mildew in zucchini squash (*Cucurbita pepo* L.) *Euphytica*, Vol. 130 (3):433-441). The heterozygous plants carrying this co-dominant gene produce a segregating ratio of 1 powdery mildew resistant plant to 2 powdery mildew tolerant plants to 1 powdery mildew susceptible plant. *C. pepo* varieties currently available exhibit a range in the level of resistance depending on whether the variety is heterozygous or homozygous for the co-dominant gene. None of the currently available commercial pumpkin varieties or the parental pumpkin varieties of the present invention, keep a consistent powdery mildew resistance level during the complete growing season. Varieties homozygous for currently available co-dominant gene usually develop somewhat less powdery mildew than those heterozygous for currently available co-dominant gene. In catalogues these varieties are often described as resistant and tolerant, respectively.

All currently available pumpkin and squash varieties designated as being powdery mildew resistant or tolerant exhibit some suppression of powdery mildew development for a few weeks, but become affected by different levels of disease severity and may die up to a month or more before the end of the complete growing season. Effective powdery mildew chemical control is therefore still needed in order to get fruit and seed production. Although chemicals such as Tosin M, Nova, FLINT, AMISTAR, QUADRIS, QUINTEC, DMI, BAYLETON, PROCURE, etc., have been used to effectively manage powdery mildew for decades, unfortunately, all such materials are at risk for the development of resistance by the various powdery mildew strains. In view of the inevitable occurrence of powdery mildew and the significant expense for disease control, breeding for better powdery mildew resistance in pumpkin and squash is very important.

Unexpectedly, the novel genetic factor of the present invention which is capable of transmitting powdery mildew resistance has been determined to be a single dominant allele which has been designated Pm2. It is a feature of the present invention that this single PMR mutant allele may be used in and transferred among the various pumpkin, squash and gourd varieties in the *C. pepo* species.

In another aspect, the present invention provides regenerable cells for use in tissue culture. The tissue culture will preferably be capable of regenerating plants having the physiological and morphological characteristics of the foregoing *C. pepo* plant, and of regenerating plants having substantially the same genotype as the foregoing *C. pepo* plant. Preferably, the regenerable cells in such tissue cultures will be embryos, protoplasts, meristematic cells, callus, pollen, leaves, anthers, pistils, stems, petioles, roots, root tips, fruits, seeds, flowers, cotyledons, hypocotyls or the like. Still further, the present invention provides *C. pepo* plants regenerated from the tissue cultures of the invention.

Another aspect of the invention is to provide methods for producing other *C. pepo* plants derived from a HSPMR7B1 plant having the Pm2 mutant allele. *C. pepo* lines derived by the use of those methods are also part of the invention.

The invention also relates to methods for producing a *C. pepo* plant containing in its genetic material one or more transgenes and to the transgenic *C. pepo* plant produced by that method.

In another aspect, the present invention provides for single or multiple gene converted plants of HSPMR7B1 carrying Pm2. The single transferred gene may preferable be a dominant or recessive allele. Preferably, the single transferred gene will confer such trait as male sterility, herbicide resistance, and insect resistance, resistance for bacterial, fungal, or viral disease, male fertility, improved harvest characteristics, enhanced nutritional quality, and improved processing characteristics. The single gene may be a naturally occurring *C. pepo* gene or a transgene introduced through genetic engineering techniques.

The invention further provides methods for developing *C. pepo* plants in a *C. pepo* plant breeding program using plant breeding techniques including recurrent selection, backcrossing, pedigree breeding, restriction fragment length polymorphism enhanced selection, genetic marker enhanced selection and transformation. *C. pepo* seeds, plants and parts thereof produced by such breeding methods are also part of the invention.

The present invention is directed to developing unique plants of *Cucurbita pepo*. The pumpkin fruit and plants of the present invention unexpectedly express a substantial increase in powdery mildew resistance. A transferable gene or allele that conveys this characteristic has been isolated and incorporated into other genetic backgrounds. The allele of the instant invention has also been expressed in different genetic backgrounds of pumpkin. To date, no commercialized *C. pepo* variety has the consistent resistance to powdery mildew conferred by the mutant allele Pm2 of the present invention. The crosses with the mutant allele Pm2 of the present invention unexpectedly expressed a unique resistance pattern during the last two years of trials, in which the plants showed a consistent strong resistance level throughout the whole growing season and without the aid of any chemical application. It would be commercially very desirable to have new varieties of C. pepo that have a better and more consistent resistance to powdery mildew for growers, the commercial market, and especially for organic growers.

As used herein, the term plant includes plant cells, plant protoplasts, plant cell tissue cultures from which C. pepo plants can be regenerated, plant calli, plant clumps and plant cells that are intact in plants, or parts of plants, such as embryos, pollen, ovules, flowers, stems, leaves, roots, root tips, anthers, pistils, and the like.

EXAMPLES

The following examples are provided to further illustrate the present invention and are not intended to limit the invention beyond the limitations set forth in the appended claims.

Example 1

Development of the Present Invention HSPMR7B1 with the PMR Mutant Allele Pm2

The mutant allele of the present invention, Pm2, unexpectedly arose from an open pollinated pumpkin plant from a research field in 2000. The series of crosses and selections is shown in Table 1. [(Howden×Coach)×Sprit] in Table 1 was a pumpkin three-way cross made between 1999 and 2000. Neither of these three parents, Hamden, Coach or Sprit, have the resistance of the allele of the present invention. The H7B-1Lop population, considered an $F_2$, was derived from a plant which exhibited strong powdery mildew resistance that was open-pollinated in the three-cross generation in the summer of 2000. During a pedigree selection process, five plants which exhibited a high level of powdery mildew resistance were selected and selfed from the $F_2$ population in 2001 and used to form the $F_3$ families H7B-1LOP-1, H7B-1LOP-2, H7B-1LOP-3, H7B-1LOP-4, and H7B-1LOP-5, respectively. In the summer of 2002, it was found that families H7B-1LOP-2, H7B-1LOP-3 and H7B-1LOP-5 all produced ratios of 3 powdery mildew resistant plants to 1 powdery mildew susceptible plant, while all the plants in the H7B-1LOP-1 family were powdery mildew resistant. Four powdery mildew plants in the H7B-1Lop-1 family and one in the H7B-1Lop-4 family were further selfed and used to form the H7B-1Lop-1-1, H7B-1Lop-1-2, H7B-1Lop-1-3, H7B-1Lop-1-4 and H7B-1Lop-4-1 families. The $F_4$ seeds were planted and the seedlings were screened with powdery mildew innocula (Sphaerotheca fuliginea Poll. and Erysiphe cichoracearum DC). The powdery mildew screening showed that all five families were non-segregating for the powdery mildew resistance trait in the fall of 2002. The $F_5$ lines, H7B-1Lop-1-1-1, H7B-1Lop-1-1-2, H7B-1Lop-1-1-3 and H7B-1Lop-4-1-1 were produced from the $F_4$ families H7B-1Lop-1-1 and H7B-1Lop-4-1 in the same season. At the same time two crosses were also made by crossing $F_4$ (H7B-1Lop-1-1) plants to a common powdery mildew susceptible pumpkin male designated 710M. Additionally, two backcrosses (BC) were made to produce BC populations for further testing during the winter of 2002. The backcrosses were (H7B-1Lop-1-1×710M)BC11 and (H7B-1Lop-1-1×710M)BC12.

Table 1 shows a summary of the series of crosses described in the previous paragraph. Column 1 shows the pedigree, column 2 shows the year for each cross, and column 3 shows remarks concerning each cross.

TABLE 1

| Pedigree | Year | Remarks |
| --- | --- | --- |
| Recombining Generation | | |
| [(Howden × Coach) × Sprit]-1L O.P. or $F_2$ Population | 1999-2000 | Designated H7B-1L |
| H7B-1Lop | 2001 | O.P. plant with strong PMR |
| $F_3$ Family | | |
| H7B-1Lop-1 | 2002 | No PMR Segregation |
| H7B-1Lop-2 | 2002 | PMR segregation, 3PMR:1PMS |
| H7B-1Lop-3 | 2002 | PMR segregation, 3PMR:1PMS |
| H7B-1Lop-4 | 2002 | No PMR segregation |
| H7B-1Lop-5 | 2002 | PMR segregation, 3PMR:1PMS |
| $F_4$ Family | | |
| H7B-1Lop-1-1 | 2002 | No PMR segregation |
| H7B-1Lop-1-2 | 2002 | No PMR segregation |
| H7B-1Lop-1-3 | 2002 | No PMR segregation |
| H7B-1Lop-1-4 | 2002 | No PMR segregation |
| H7B-1Lop-4-1 | 2002 | No PMR segregation |
| $F_5$ Family | | |
| H7B-1Lop-1-1-1 | 2003 | No PMR segregation |
| H7B-1Lop-1-1-2 | 2003 | No PMR segregation |
| H7B-1Lop-1-1-3 | 2003 | No PMR segregation |
| H7B-1Lop-4-1-1 | 2003 | No PMR segregation |
| Test Crosses & Backcrosses | | |
| H7B-1Lop-1-1 × 710M | 2002 | |
| (H7B-1Lop-1-1 × 710M)BC11 | 2002 | PMR segregation, 1PMR:1PMS |
| (H7B-1Lop-1-1 × 710M)BC12 | 2002 | PMR segregation, 1PMR:1PMS |
| $F_1$ Hybrids | | |
| H7B-1Lop-1-1-1 × BSP1 | 2002 | Designated HSR4706, PMR |
| H7B-1Lop-1-1-1 × GDF41 | 2002 | Designated HSR4707, PMR |
| H7B-1Lop-1-1-1 × HDD31 | 2002 | Designated HSR4709, PMR |

Example 2

Determining the Genetic Relation of the PMR Mutant Allele Pm2 in the Invention and Powdery Mildew Susceptible Allele pm in Commercial Varieties To determine the genetic mechanism of the new powdery mildew resistance characteristic of the present invention, five $F_3$ families were produced and planted in the summer of 2002. These five $F_3$ families were produced by selecting and selfing five plants from the $F_2$ population in 2001. The $F_3$ families produced from the selected five plants were designated H7B-1LOP-1, H7B-1LOP-2, H7B-1LOP-3, H7B-1LOP-4, and H7B-1LOP-5, respectively. It was found that families H7B-1LOP-2, H7B-1LOP-3 and H7B-1LOP-5 all produced ratios of 3 powdery mildew resistant plants to 1 powdery mildew susceptible plant however plants in the H7B-1LOP-1 family were all powdery mildew resistant. Upon comparison of comprehensive characteristics among the families, it was found that families H7B-1Lop-2, H7B-1Lop-3 and H7B-1Lop-5 were not ideal in either fruit traits or plant habits and thus, these families were not used in further breeding efforts. The H7B-1LOP-1 family or line was named as HSPMR7B1.

The two remaining families, H7B-1Lop-1 and H7B-1Lop-4, had desirable fruit characteristics, therefore four plants of the H7B-1Lop-1 family and one plant of the H7B-1Lop-4 family were selected and selfed to form H7B-1Lop-1-1, H7B-

1Lop-1-2, H7B-1Lop-1-3, H7B-1Lop-1-4 and H7B-1Lop-4-1, respectively. The resulting $F_4$ seeds were planted and the seedlings were screened with powdery mildew inocula (*Sphaerotheca fuliginea* Poll. and *Erysiphe cichoracearum* DC). The powdery mildew screening showed that all five $F_4$ families were non-segregating for the powdery mildew resistance trait in the fall of 2002. Of the $F_4$ families, two were kept for advanced selections of other traits except for powdery mildew. The $F_5$ families, H7B-1Lop-1-1-1, H7B-1Lop-1-1-2, H7B-1Lop-1-1-3 and H7B-1Lop-4-1-1 were produced from the 2002 season. At the same time two crosses were also made by crossing $F_4$ (H7B-1Lop-1-1) plants to a common powdery mildew susceptible pumpkin male designated 710M. Additionally, two backcrosses (BC) were made to produce BC populations for further testing during the winter of 2002. The backcrosses were (H7B-1Lop-1-1×710M)BC11 and (H7B-1Lop-1-1×710M)BC12. The two BC populations were tested and both segregated 1 powdery mildew resistant plant to 1 powdery mildew susceptible plant during the summer 2003.

The data, as shown in Table 2, indicated that, except for the H7B-1LOP-1 family, all four other families had a heterozygous genotype and that the powdery mildew resistance phenotype of the present invention is under the control of a single dominant allele designated Pm2. Table 2 shows the genetic mechanism of the new powdery mildew characteristic. Column 1 shows the pumpkin family, column 2 shows the number of plants in that family displaying the powdery mildew resistant phenotype, column 3 shows the number of plants in that family displaying the powdery mildew susceptible phenotype, and columns 4 and 5 show the Chi-square analysis of the data. "z" means that all $X^2$ are non significant at 0.01 probability and the PMR and PMS segregation meet 3:1 and "-- --" means not tested.

TABLE 2

PMR Segregation In Six Selfed And BC Families

| | | | Chi-square$^z$ | |
|---|---|---|---|---|
| Family | PMR | PMS | $X^2$(3:1) | $X^2$(1:1) |
| $F_3$ Families | | | | |
| H7B-1Lop-1 | 55 | 0 | — | — |
| H7B-1Lop-2 | 37 | 13 | 0.0267 | — |
| H7B-1Lop-3 | 47 | 16 | 0.0053 | — |
| H7B-1Lop-4 | 28 | 9 | 0.0090 | — |
| H7B-1Lop-5 | 31 | 11 | 0.032 | — |
| BC Populations | | | | |
| (H7B-1Lop-1-1 × 710M)BC11 | 19 | 17 | — | 0.1111 |
| ((H7B-1Lop-1-1 × 710M)BC12 | 24 | 27 | — | 0.1765 |

Example 3

Determining the Genetic Relation of the PMR Mutant Allele Pm2 in the Present Invention and an Existing Powdery Mildew Resistant Allele Pm in Commercial Varieties The genetic relation between Pm and Pm2 was also tested in 2008 and 2009. Three crosses were made in the greenhouse in the spring of 2008 with a descendant line of the present invention HSPMR7B1, "H7BFlat-1", carrying Pm2, and three lines lodged with Pm, MlnF411, MltnF42-1 and HKN89-3R-1(op)-1-1, which were derived from the commercial varieties Merlin, Magic Lantern and a breeding material of Cornell University. The three crosses, H7BFlat-1×MlnF411, H7BFlat-1×MltnF42-1 and H7BFlat-1×HKN89-3R-1(op)-1-1, were tested in Hollar's 2008 summer trial in Rocky Ford, Colo. The experiment was engaged in a completely randomized way with two replications, in which the aforementioned four parental lines and a commercial powdery mildew susceptible variety, Frosty, were taken as comparisons. All the experimental entries were planted on May 15 and observation on powdery mildew was not made until August because the disease would usually not occur in the fields during the early growing season. The incidence of powdery mildew on plants was still divided into six scores or categories consisting of 0, 1, 2, 3, 4, 5, in which 0 indicates that the plants are completely resistant to the disease and there are no symptoms of the disease on the plants at all; and a rating of 5 indicates that the plants are 100% infected and susceptible. The powdery mildew resistance data was collected on Sep. 10, 2008 when the powdery mildew symptom of the pumpkin plants was most distinguishable. Compared to the powdery mildew resistance among all entries, H7BFlat-1, H7BFlat-1×MlnF411 and H7BFlat-1×MltnF42-1 had the strongest resistance that almost reached an immune level; the parental lines MlnF411, MltnF42-1 and HKN89-3R-1(op)-1-1 showed a significantly lower level than the former three, but are still in a strong resistant category; the resistance of the cross H7BFlat-1×HKN89-3R-1(op)-1-1 was on the strong side of the intermediate level of its parent lines; and Frosty had completely come down with the powdery mildew disease (Table 3). At the same time, the F2 seeds of the three crosses were generated in the Hollar green house. The resistant segregation of the three populations was further tested in the greenhouse in the fall of 2008 and the summer of 2009 (Table 4). Although the difference of the powdery mildew resistant levels between the plants of the present invention containing the Pm2 mutant allele (Pm2Pm2 and Pm2Pm) and the common resistant plants (PmPm) was much smaller than in between all the resistant plants (Pm2Pm2, Pm2Pm and PmPm) and the susceptible comparison (pmpm), the test result showed that the inheritance of Pm2, Pm and pm is similar to the genetic mechanism of *C. pepo* fruit color genes in which a dominant white color gene (W) is dominant to a green color (C) which is further dominant to a recessive white color (w) and etc. In spite of variations of the $F_2$ populations in the greenhouse and field, the Chi-square scores indicated that the segregation ratio of the PMR mutant plants (Pm2Pm2 and Pm2Pm) and the common resistant plants (PmPm) in all tested $F_2$ population is not significant from 3:1 at 0.01 level. It can be concluded that the PMR mutant allele Pm2 is simply dominant to the allele Pm and both of them are dominant to the recessive allele pm. In Table 3, "y" means the incidence of powdery mildew is divided five levels in which 0 stands for complete resistance (or immunity) and 5 for complete susceptibility and "z" means all means with the same letter are not significantly different; those with the different letters are significantly different at 0.01 probability. In Table 4, "z" means that all $X^2$ are non significant at 0.01 probability and the Pm2Pm2 and PmPm segregation meet 3:1.

TABLE 3

Assessment Of Pm2 And Pm Expression In The Parent Lines And $F_1$ In 2008

| Tested Entries | Replication | Incidence of powdery mildew$^y$ (20 plants) | Mean$^z$ |
|---|---|---|---|
| Frosty (pmpm) | I | 5.0 4.5 5.0 5.0 5.0 5.0 4.5 5.0 5.0 5.0<br>4.5 5.0 5.0 5.0 5.0 5.0 5.0 5.0 5.0 5.0 | |
| | II | 5.0 5.0 5.0 5.0 5.0 5.0 5.0 5.0 5.0 5.0<br>5.0 5.0 5.0 4.5 5.0 5.0 5.0 5.0 4.5 5.0 | 4.9375a |
| MltnF42-1 (Pm line) | I | 2.0 2.5 2.5 2.5 3.0 3.0 1.5 2.5 2.5 2.0<br>1.5 1.5 3.0 2.5 2.0 2.0 2.5 2.0 2.0 2.5 | |
| | II | 2.5 3.0 2.0 3.0 2.5 2.0 2.5 3.0 2.5 2.0<br>3.0 2.5 2.5 2.0 2.0 2.5 2.5 2.0 2.0 3.0 | 2.3625b |
| MlnF411 (Pm line) | I | 2.5 1.5 2.5 1.5 2.0 2.5 1.5 2.0 2.0 2.0<br>1.5 3.0 1.5 2.0 2.5 2.0 2.0 2.5 1.0 2.0 | |
| | II | 2.0 2.5 2.5 1.5 2.0 1.5 2.5 2.5 3.0 1.5<br>1.5 2.0 2.5 2.5 2.5 2.0 1.5 2.0 2.5 2.5 | 2.3250b |
| HKN89-3R-1(op)-1-1 (Pm line) | I | 2.5 1.5 2.5 1.5 2.0 2.5 1.5 2.0 2.0 2.0<br>1.5 3.0 1.5 2.0 2.5 2.0 2.0 2.5 1.0 2.0 | |
| | II | 2.0 2.5 2.5 1.5 2.0 1.5 2.5 2.5 3.0 1.5<br>1.5 2.0 2.5 2.5 2.5 2.0 1.5 2.0 2.5 2.5 | 2.0875c |
| H7BFlat-1 × HKN89-3R-1(op)-1-1 | I | 1.5 0.5 1.0 0.0 0.5 0.0 0.5 1.0 0.0 0.0<br>0.5 2.0 1.0 1.5 0.0 0.5 0.0 1.0 0.0 0.5 | |
| | II | 1.0 0.0 0.0 2.0 2.0 0.0 0.0 0.0 0.5 1.0<br>1.0 0.0 2.0 1.5 0.0 0.0 1.0 1.0 0.5 0.0 | 0.6375d |
| H7BFlat-1 × MlnF411 | I | 0.0 0.5 0.5 0.5 1.0 0.0 0.5 0.0 0.5 0.0<br>0.5 1.0 0.0 0.5 0.0 0.0 1.0 0.0 0.0 0.5 | |
| | II | 0.5 0.0 1.0 0.5 0.5 0.0 0.5 0.0 0.5 0.0<br>1.0 0.0 0.0 0.5 0.0 0.0 0.5 0.0 0.5 1.0 | 0.3500e |
| H7BFlat-1 × MtlnF42-1 | I | 0.5 0.5 0.0 0.0 0.5 0.0 0.5 0.0 0.0 0.5<br>0.5 0.0 1.0 0.5 0.0 0.5 0.0 1.0 0.0 0.5 | |
| | II | 0.0 0.0 0.0 0.5 0.5 0.5 0.0 0.0 1.0 0.5 0.0<br>0.5 0.0 0.0 0.5 1.0 0.5 0.0 0.5 0.0 0.0 | 0.3250e |
| H7BFlat-1 (Pm2 line) | I | 0.0 0.5 0.5 0.0 0.5 1.0 0.0 0.0 0.5 0.0<br>0.5 0.0 0.5 0.5 0.0 0.0 0.0 0.5 0.5 0.0 | |
| | II | 0.5 0.0 1.0 0.0 0.5 0.5 0.5 0.0 0.5 0.0<br>0.5 0.0 0.0 0.5 0.0 0.0 1.0 0.5 0.0 0.0 | 0.2875e |

TABLE 4

Inheritance Of Pm2 And Pm In $F_2$ Populations In 2009
PMR Segregation In Three $F_2$ Populations

| | Pm2Pm2 | PmPm | Chi-square$^z$ $X^2(3:1)$ |
|---|---|---|---|
| $F_2$ populations in greenhouse | | | |
| (H7BFlat-1 × MltnF42-1)$F_2$ | 67 | 27 | 0.6950 |
| (H7BFlat-1 × MlnF411)$F_2$ | 64 | 25 | 0.4532 |
| (H7BFlat-1 × HKN89-3R-1(op)-1-1)$F_2$ | 70 | 29 | 0.9731 |
| $F_2$ populations in Field | | | |
| (H7BFlat-1 × MltnF42-1)$F_2$ | 20 | 10 | 1.1111 |
| (H7BFlat-1 × MlnF411)$F_2$ | 21 | 11 | 1.5000 |
| (H7BFlat-1 × HKN89-3R-1(op)-1-1)$F_2$ | 18 | 10 | 1.7143 |

Example 4

Assessing the Level of Powdery Mildew Resistance Conferred by the Mutant Allele Pm2 of the Present Invention in Hybrid Form Comparing with Commercial Varieties Having Pm 2005 Trial Using Drip Irrigation:

To assess the powdery mildew resistance level conferred by the mutant allele Pm2 of the present invention in hybrid form, three selected commercially available powdery mildew susceptible pumpkin lines BSP1, GDF41, and HDD31 were crossed with the powdery mildew resistant line H7B-1Lop-1-1-1 which contains the mutant allele Pm2 of the present invention, respectively, and formed three hybrids, HSR4706, HSR4707 and HSR4709 in 2004. These hybrids each contain the mutant allele Pm2 of the present invention and were tested for powdery mildew resistance successively in experimental trials during the summers of 2005 and 2006. The level of powdery mildew on plants was divided into six scores or fractions thereof consisting of 0, 1, 2, 3, 4, 5, in which 0 indicates that the plants were completely resistant to the disease and there were no symptoms of the disease on the plants at all, and a rating of 5 indicates that the plants were 100% infected and susceptible. Increasing one level among the six scores means that the resistance to powdery mildew disease decreased by 20% or, conversely, the susceptibility to the disease increased by 20%. For example, a plant with a score of 1 means that plant showed 20% more disease symptoms than a plant with a score of 0. In another example, a plant with a score of 3 means that plant shows 60% more disease symptoms than a plant with a score of 0. Each score is based on the following: the ratio of infected leaves and stems on a plant, the proportion of infected area on a leaf and a stem, and the colony counts out of the total in the infected area. To facilitate the difference among the powdery mildew resistance levels for analysis, a significance test reciprocal transformation was applied during the mean separation process.

The first powdery mildew resistance pumpkin hybrid trial was conducted in the summer of 2005. The experiment was designed to determine whether the new powdery mildew resistance characteristic conferred by the mutant allele Pm2 of the present invention in hybrids is superior to that of what is available in commercial pumpkin varieties. The new hybrids containing the mutant allele Pm2 were HSR4706, HSR4707, and HSR4709. These hybrids were produced from the cross between the homozygous PMR line H7B-1Lop-1-1-1, which contained the mutant allele Pm2 of the present invention, and a commercially available powdery mildew susceptible male. Three commercial varieties, Merlin, Magic Lantern and Spartan, which were considered the best commercially available powdery mildew resistant varieties at that time, were used for comparison. A completely randomized experimental design with two replications was used for each treatment and each treatment consisted of 60 plants grown 36 inches apart within a row covered with plastic mulch and 80 inches between the rows. An underground drip irrigation system accompanying a routine fertilizer supply was used. The trial time period started with direct seeding on May 15, 2005 and was kept as long as possible to allow for a full expression of powdery mildew resistance and plant growth potential in all the tested varieties.

In Table 5, the results of the powdery mildew resistance trial for 2005 are shown. Column 1 shows the variety, column 2 shows the replication, and column 3 shows the mean powdery mildew resistance reading based on the scores of 30 plants per replication. Means were transformed and analyzed using an F test on the transformed mean of the average powdery mildew resistance reading. Means (analyzed as transformed means) bearing the same letters indicate those means that were not significantly different at the 1% level.

As shown in Table 5, the three pumpkin varieties containing the mutant allele Pm2 of the present invention had mean scores of about 1.3 while the three commercially available pumpkin varieties had mean scores of about 3.1. These results indicate that the pumpkin varieties containing the mutant allele Pm2 were highly resistant to powdery mildew, whereas the commercial pumpkin varieties were only slightly to moderately resistant.

TABLE 5

PMR Scores

| Variety | Rep | Mean |
| --- | --- | --- |
| HSR4706 | I | 1.2833 |
|  | II | 1.3167 |
|  | Overall | 1.3000a |
| HSR4707 | I | 1.3667 |
|  | II | 1.2833 |
|  | Overall | 1.3334a |
| HSR4709 | I | 1.3333 |
|  | II | 1.3500 |
|  | Overall | 1.3417a |
| Spartan | I | 2.9667 |
|  | II | 3.0333 |
|  | Overall | 3.0000b |
| Magic Lantern | I | 3.1333 |
|  | II | 3.1500 |
|  | Overall | 3.1417b |
| Merlin | I | 3.1500 |
|  | II | 3.3000 |
|  | Overall | 3.225b |

2006 Trial Using a Furrowed Irrigation System:

The second pumpkin trial for powdery mildew resistance was carried out in the summer of 2006 and had the same experimental design and field lay-out as in the previous 2005 trial. This time, there was no plastic mulch and no drip system was used. Instead, furrow irrigation was used for the trial so that it could make the ground surface as moist as possible to cause the occurrence of powdery mildew.

The level of powdery mildew on plants was divided into six scores or fractions thereof consisting of 0, 1, 2, 3, 4, 5, in which 0 indicates that the plants were completely resistant to the disease and there were no symptoms of the disease on the plants at all, and a rating of 5 indicates that the plants were 100% infected. Increasing one level among the six scores, means that the resistance to the disease decreased by 20% or, conversely, the susceptibility to the disease increased by 20%. For example, a plant with a score of 1 means that plant showed 20% more disease symptoms than a plant with a score of 0. In another example, a plant with a score of 3 means that plant shows 60% more disease symptoms than a plant with a score of 0. Each score is based on the following: the ratio of infected leaves and stems on a plant, the proportion of infected area on a leaf and a stem, and the colony counts out of the total in the infected area. To better understand the difference among the PMR levels, a significance test reciprocal transformation was applied during the mean separation process.

In Table 6, the results of the powdery mildew resistance trial for 2006 are shown. Column 1 shows the variety, column 2 shows the replication, and column 3 shows the mean powdery mildew resistance reading based on the scores of 30 plants per replication. Means were transformed and analyzed using an F test on the transformed mean of the average powdery mildew resistance reading. Means (analyzed as transformed means) bearing the same letters indicate those means that were not significantly different at the 1% level.

As shown in Table 6, the three varieties containing the mutant allele Pm2 had mean powdery mildew resistance scores of about 1.4 while the commercially available pumpkin varieties had mean scores of about 3.4. These results indicate that the pumpkin varieties containing the mutant allele Pm2 were highly resistant to powdery mildew, whereas the commercial pumpkin varieties were moderately to slightly resistant. These scores also show that the mutant allele Pm2 continued to provide the pumpkin plants containing the allele with powdery mildew resistance under increased powdery mildew pressure, whereas the commercially available pumpkin varieties were more heavily affected by the increased powdery mildew presence.

TABLE 6

| Variety | Rep | Mean |
| --- | --- | --- |
| HSR4706 | I | 1.3833 |
|  | II | 1.4167 |
|  | Overall | 1.3917a |
| HSR4707 | I | 1.4333 |
|  | II | 1.3833 |
|  | Overall | 1.4083a |
| HSR4709 | I | 1.4167 |
|  | II | 1.4500 |
|  | Overall | 1.4250a |
| Spartan | I | 3.2500 |
|  | II | 3.2667 |
|  | Overall | 3.2583b |
| Magic Lantern | I | 3.3667 |
|  | II | 3.3833 |
|  | Overall | 3.3750b |
| Merlin | I | 3.3833 |
|  | II | 3.4500 |
|  | Overall | 3.4167b |

The powdery mildew screening tests showed that all of the pumpkin plants containing the mutant allele Pm2 of the present invention unexpectedly had much greater resistance to powdery mildew than any of the commercial pumpkin varieties in the two preceding trials from 2005 and 2006. Unexpectedly, when the commercial pumpkin varieties began to die by the beginning of September because of powdery mildew infection, all of the pumpkin plants containing the mutant allele Pm2 of the present invention continued to grow and bear fruit until the first killing frost occurred. The phenotypic expression of the new powdery mildew mutant allele Pm2 in the new pumpkin hybrids was unexpectedly found to be more than two times greater than the powdery mildew resistance displayed by the commercial varieties based on the differences between the means in Tables 5 and 6. Statistical results in Tables 5 and 6 show that the powdery mildew resistance levels between the new pumpkin hybrids containing the mutant allele Pm2 of the present invention and the powdery mildew resistance levels of the commercial pumpkin varieties were significantly different ($F_{0.01}$). The powdery mildew resistance exhibited by the new varieties, which contain the mutant allele Pm2 of the present invention, is significantly better than the powdery mildew resistance exhibited by currently available commercial varieties.

2007 Trial for Powdery Mildew Resistance (Trial 5):

The third pumpkin trial for powdery mildew resistance was carried out in the summer of 2007 and the data was collected on Aug. 15, 2007 and Sep. 15, 2007. To determine the differences in powdery mildew resistance (PMR) between pumpkin plants of the present invention containing the Pm2 allele and commercial pumpkin varieties, the trial was conducted in southern Colorado with a randomized block layout, which adopted two replications and used leaves, petioles and stems as three treatments for the objective of investigating the degree of powdery mildew infection. Due to the continuous dying-off of the commercial plants Merlin, Magic Lantern and Spartan during the growing season, the missed plants in each plot were left out and only the truncated data that was collected on Aug. 15, 2007 (Table 7) from the first six survived plants was used in the statistical analyses. The data (Table 8) from Sep. 15, 2007 was not statistically analyzed because most of the observed plants of some commercial varieties were lost due (died) to the powdery mildew infection during the growing season and is just used for general information herein.

The level of powdery mildew on plants was counted as the mean number powdery mildew colonies found per square inch on a leaf, petiole or stem of the pumpkin plant. The plants were about 90 days old.

Table 7 shows the data of the powdery mildew resistance trial collected from the pumpkin varieties of the present invention, HSR4706, HSR4707, HSR4709 HSR4710, HSR4711 and HSR4720, with commercial pumpkin varieties Merlin, Magic Lantern and Spartan on Aug. 15, 2007. Table 7 consists of two blocks (I and II). Column 1 shows the variety, column 2 shows the replication, column 3 shows the observed organs as three treatments (leaf, stem, and petiole), and column 4 shows the mean number of colonies of powdery mildew per square inch on a particular plant organ (leaf, petiole, or stem), which is derived from 10 plants listed in the 10 sub-columns. Each entry in the 10 sub-columns represents the mean number of colony counts on different locations of observed plant parts (the leaf, petiole, or stem) from each individual plant. Entries that do not contain a number (blank cells) mean that the plants did not survive (died) during the trial.

TABLE 7

| Trial Entries | Reps | Observed Organs | Mean Colonies/inch$^2$ Group (weeks after planting) | | | | | | | | | |
|---|---|---|---|---|---|---|---|---|---|---|---|---|
| | | | 1 | 2 | 3 | 4 | 5 | 6 | 7 | 8 | 9 | 10 |
| Block I | | | | | | | | | | | | |
| HSR4710 | 1 | Leaf | 0 | 0 | 0 | 0 | 0 | 0 | 1 | 0 | 0 | |
| | | Petiole | 0 | 0 | 0 | 0 | 0 | 0 | 0 | 0 | 0 | |
| | | Stem | 0 | 0 | 0 | 0 | 0 | 0 | 0 | 0 | 0 | |
| | 2 | Leaf | 0 | 1 | 0 | 0 | 1 | 0 | 0 | 0 | | |
| | | Petiole | 0 | 0 | 0 | 0 | 0 | 0 | 0 | 0 | | |
| | | Stem | 0 | 0 | 0 | 0 | 0 | 0 | 0 | 0 | | |
| Merlin | 1 | Leaf | 4 | 6 | 5 | 5 | 5 | 6 | 5 | | | |
| | | Petiole | 2 | 2 | 4 | 4 | 3 | 3 | 4 | | | |
| | | Stem | 1 | 1 | 3 | 2 | 3 | 3 | 2 | | | |
| | 2 | Leaf | 4 | 5 | 6 | 4 | 5 | 6 | | | | |
| | | Petiole | 1 | 2 | 4 | 4 | 3 | 3 | | | | |
| | | Stem | 3 | 2 | 2 | 3 | 3 | 3 | | | | |
| HSR4706 | 1 | Leaf | 0 | 0 | 0 | 0 | 1 | 0 | 0 | 0 | | |
| | | Petiole | 0 | 0 | 0 | 0 | 0 | 0 | 0 | 0 | | |
| | | Stem | 0 | 0 | 0 | 0 | 0 | 0 | 0 | 0 | | |
| | 2 | Leaf | 0 | 0 | 2 | 0 | 0 | 0 | 0 | 0 | 0 | |
| | | Petiole | 0 | 0 | 0 | 0 | 0 | 0 | 0 | 0 | 0 | |
| | | Stem | 0 | 0 | 0 | 0 | 0 | 0 | 0 | 0 | 0 | |
| HSR4720 | 1 | Leaf | 0 | 0 | 0 | 0 | 0 | 0 | 0 | 0 | | |
| | | Petiole | 0 | 0 | 0 | 0 | 0 | 0 | 0 | 0 | | |
| | | Stem | 0 | 0 | 0 | 0 | 0 | 0 | 0 | 0 | | |
| | 2 | Leaf | 0 | 0 | 0 | 0 | 0 | 0 | 0 | 0 | 0 | |
| | | Petiole | 0 | 0 | 0 | 0 | 0 | 0 | 0 | 0 | 0 | |
| | | Stem | 0 | 0 | 0 | 0 | 0 | 0 | 0 | 0 | 0 | |
| Magic Lantern | 1 | Leaf | 2 | 2 | 3 | 4 | 4 | 4 | 3 | | | |
| | | Petiole | 1 | 2 | 2 | 1 | 3 | 2 | 2 | | | |
| | | Stem | 1 | 1 | 1 | 2 | 2 | 2 | 1 | | | |
| | 2 | Leaf | 4 | 3 | 3 | 5 | 4 | 4 | | | | |
| | | Petiole | 2 | 1 | 1 | 3 | 2 | 2 | | | | |
| | | Stem | 2 | 1 | 1 | 2 | 2 | 2 | | | | |
| HSR4707 | 1 | Leaf | 0 | 0 | 0 | 0 | 1 | 0 | 0 | 0 | | |
| | | Petiole | 0 | 0 | 0 | 0 | 0 | 0 | 0 | 0 | | |
| | | Stem | 0 | 0 | 0 | 0 | 0 | 0 | 0 | 0 | | |
| | 2 | Leaf | 1 | 0 | 0 | 0 | 0 | 0 | 0 | 0 | 0 | |
| | | Petiole | 0 | 0 | 0 | 0 | 0 | 0 | 0 | 0 | 0 | |
| | | Stem | 0 | 0 | 0 | 0 | 0 | 0 | 0 | 0 | 0 | |

TABLE 7-continued

| Trial Entries | Reps | Observed Organs | Mean Colonies/inch$^2$ Group (weeks after planting) | | | | | | | | | |
|---|---|---|---|---|---|---|---|---|---|---|---|---|
| | | | 1 | 2 | 3 | 4 | 5 | 6 | 7 | 8 | 9 | 10 |
| Spartan | 1 | Leaf | 3 | 3 | 2 | 4 | 4 | 3 | | | | |
| | | Petiole | 3 | 1 | 1 | 2 | 3 | 2 | | | | |
| | | Stem | 1 | 2 | 2 | 2 | 3 | 2 | | | | |
| | 2 | Leaf | 3 | 3 | 3 | 4 | 3 | 3 | | | | |
| | | Petiole | 3 | 1 | 2 | 3 | 3 | 2 | | | | |
| | | Stem | 2 | 3 | 2 | 2 | 2 | 2 | | | | |
| HSR4709 | 1 | Leaf | 0 | 0 | 0 | 0 | 0 | 0 | 0 | 1 | 0 | 0 |
| | | Petiole | 0 | 0 | 0 | 0 | 0 | 0 | 0 | 0 | 0 | 0 |
| | | Stem | 0 | 0 | 0 | 0 | 0 | 0 | 0 | 0 | 0 | 0 |
| | 2 | Leaf | 0 | 0 | 1 | 0 | 0 | 0 | 0 | 0 | 0 | 0 |
| | | Petiole | 0 | 0 | 0 | 0 | 0 | 0 | 0 | 0 | 0 | 0 |
| | | Stem | 0 | 0 | 0 | 0 | 0 | 0 | 0 | 0 | 0 | 0 |
| HSR4711 | 1 | Leaf | 0 | 0 | 0 | 1 | 0 | 0 | 0 | 1 | 0 | 0 |
| | | Petiole | 0 | 0 | 0 | 0 | 0 | 0 | 0 | 0 | 0 | 0 |
| | | Stem | 0 | 0 | 0 | 0 | 0 | 0 | 0 | 0 | 0 | 0 |
| | 2 | Leaf | 0 | 0 | 0 | 0 | 0 | 0 | 1 | 0 | 0 | 1 |
| | | Petiole | 0 | 0 | 0 | 0 | 0 | 0 | 0 | 0 | 0 | 0 |
| | | Stem | 0 | 0 | 0 | 0 | 0 | 0 | 0 | 0 | 0 | 0 |
| | | | Block II | | | | | | | | | |
| HSR4709 | 1 | Leaf | 0 | 0 | 0 | 2 | 0 | 0 | 0 | 0 | 0 | 1 |
| | | Petiole | 0 | 0 | 0 | 0 | 0 | 0 | 0 | 0 | 0 | 0 |
| | | Stem | 0 | 0 | 0 | 0 | 0 | 0 | 0 | 0 | 0 | 0 |
| | 2 | Leaf | 0 | 0 | 1 | 0 | 1 | 0 | 0 | | | |
| | | Petiole | 0 | 0 | 0 | 0 | 0 | 0 | 0 | | | |
| | | Stem | 0 | 0 | 0 | 0 | 0 | 0 | 0 | | | |
| HSR4710 | 1 | Leaf | 0 | 1 | 0 | 0 | 0 | 0 | 0 | 1 | 0 | 0 |
| | | Petiole | 0 | 0 | 0 | 0 | 0 | 0 | 0 | 0 | 0 | 0 |
| | | Stem | 0 | 0 | 0 | 0 | 0 | 0 | 0 | 0 | 0 | 0 |
| | 2 | Leaf | 1 | 0 | 0 | 0 | 0 | 0 | 0 | 0 | 0 | 0 |
| | | Petiole | 0 | 0 | 0 | 0 | 0 | 0 | 0 | 0 | 0 | 0 |
| | | Stem | 0 | 0 | 0 | 0 | 0 | 0 | 0 | 0 | 0 | 0 |
| Magic Lantern | 1 | Leaf | 4 | 4 | 4 | 2 | 3 | 3 | 3 | | | |
| | | Petiole | 3 | 3 | 3 | 3 | 2 | 3 | 3 | | | | |
| | | Stem | 2 | 2 | 3 | 3 | 3 | 2 | 3 | | | | |
| | 2 | Leaf | 4 | 4 | 3 | 3 | 4 | 4 | 3 | | | |
| | | Petiole | 4 | 3 | 3 | 3 | 3 | 3 | 2 | | | |
| | | Stem | 3 | 3 | 3 | 3 | 2 | 3 | 3 | | | |
| HSR4707 | 1 | Leaf | 0 | 0 | 0 | 0 | 1 | 0 | 0 | 0 | 0 | 0 |
| | | Petiole | 0 | 0 | 0 | 0 | 0 | 0 | 0 | 0 | 0 | 0 |
| | | Stem | 0 | 0 | 0 | 0 | 0 | 0 | 0 | 0 | 0 | 0 |
| | 2 | Leaf | 1 | 0 | 2 | 0 | 0 | 0 | 0 | 0 | 0 | |
| | | Petiole | 0 | 0 | 0 | 0 | 0 | 0 | 0 | 0 | 0 | |
| | | Stem | 0 | 0 | 0 | 0 | 0 | 0 | 0 | 0 | 0 | |
| Spartan | 1 | Leaf | 3 | 3 | 3 | 4 | 3 | 3 | 4 | | | |
| | | Petiole | 3 | 3 | 2 | 3 | 3 | 3 | 3 | | | |
| | | Stem | 2 | 3 | 2 | 3 | 2 | 2 | 3 | | | |
| | 2 | Leaf | 2 | 2 | 4 | 3 | 2 | 3 | 4 | | | |
| | | Petiole | 3 | 2 | 2 | 2 | 2 | 3 | 2 | | | |
| | | Stem | 2 | 2 | 2 | 2 | 3 | 2 | 3 | | | |
| HSR4720 | 1 | Leaf | 0 | 0 | 0 | 0 | 0 | 0 | 0 | 0 | 0 | |
| | | Petiole | 0 | 0 | 0 | 0 | 0 | 0 | 0 | 0 | 0 | |
| | | Stem | 0 | 0 | 0 | 0 | 0 | 0 | 0 | 0 | 0 | |
| | 2 | Leaf | 0 | 0 | 0 | 0 | 0 | 0 | 0 | 0 | 0 | |
| | | Petiole | 0 | 0 | 0 | 0 | 0 | 0 | 0 | 0 | 0 | |
| | | Stem | 0 | 0 | 0 | 0 | 0 | 0 | 0 | 0 | 0 | |
| HSR4706 | 1 | Leaf | 0 | 1 | 0 | 0 | 0 | 0 | 0 | 0 | 0 | |
| | | Petiole | 0 | 0 | 0 | 0 | 0 | 0 | 0 | 0 | 0 | |
| | | Stem | 0 | 0 | 0 | 0 | 0 | 0 | 0 | 0 | 0 | |
| | 2 | Leaf | 0 | 1 | 1 | 0 | 0 | 0 | 0 | 0 | 0 | |
| | | Petiole | 0 | 0 | 0 | 0 | 0 | 0 | 0 | 0 | 0 | |
| | | Stem | 0 | 0 | 0 | 0 | 0 | 0 | 0 | 0 | 0 | |
| Merlin | 1 | Leaf | 3 | 3 | 3 | 4 | 4 | 3 | | | | |
| | | Petiole | 3 | 3 | 2 | 4 | 3 | 2 | | | | |
| | | Stem | 2 | 3 | 3 | 3 | 2 | 3 | | | | |
| | 2 | Leaf | 4 | 3 | 4 | 4 | 3 | 4 | | | | |
| | | Petiole | 3 | 3 | 3 | 4 | 4 | 3 | | | | |
| | | Stem | 4 | 3 | 3 | 3 | 2 | 3 | | | | |
| HSR4711 | 1 | Leaf | 0 | 0 | 0 | 0 | 0 | 0 | 2 | 0 | | |
| | | Petiole | 0 | 0 | 0 | 0 | 0 | 0 | 0 | 0 | | |
| | | Stem | 0 | 0 | 0 | 0 | 0 | 0 | 0 | 0 | | |
| | 2 | Leaf | 0 | 0 | 0 | 0 | 1 | 0 | 0 | 0 | 1 | |
| | | Petiole | 0 | 0 | 0 | 0 | 0 | 0 | 0 | 0 | 0 | |
| | | Stem | 0 | 0 | 0 | 0 | 0 | 0 | 0 | 0 | 0 | |

TABLE 8

| Trial Entries | Reps | Observed Organs | Mean Colonies/inch² Group (weeks after planting) | | | | | | | | | |
|---|---|---|---|---|---|---|---|---|---|---|---|---|
| | | | 1 | 2 | 3 | 4 | 5 | 6 | 7 | 8 | 9 | 10 |
| Block I | | | | | | | | | | | | |
| HSR4710 | 1 | Leaf | 0 | 0 | 1 | 0 | 0 | 0 | 1 | 0 | 0 | |
| | | Petiole | 0 | 0 | 0 | 0 | 0 | 0 | 0 | 0 | 0 | |
| | | Stem | 0 | 0 | 0 | 0 | 0 | 0 | 0 | 0 | 0 | |
| | 2 | Leaf | 0 | 1 | 0 | 0 | 1 | 0 | 0 | | | |
| | | Petiole | 0 | 0 | 0 | 0 | 0 | 0 | 0 | | | |
| | | Stem | 0 | 0 | 0 | 0 | 0 | 0 | 0 | | | |
| Merlin | 1 | Leaf | 5 | 6 | | | | | | | | |
| | | Petiole | 2 | 3 | | | | | | | | |
| | | Stem | 1 | 2 | | | | | | | | |
| Merlin | 1 | Leaf | 1 | 0 | 0 | 0 | 1 | 0 | 0 | 0 | | |
| | | Petiole | 0 | 0 | 0 | 0 | 0 | 0 | 0 | 0 | | |
| | | Stem | 0 | 0 | 0 | 0 | 0 | 0 | 0 | 0 | | |
| | 2 | Leaf | 5 | 5 | | | | | | | | |
| | | Petiole | 2 | 3 | | | | | | | | |
| | | Stem | 3 | 3 | | | | | | | | |
| HSR4706 | 1 | Leaf | 0 | 0 | 0 | 0 | 1 | 0 | 0 | 0 | | |
| | | Petiole | 0 | 0 | 0 | 0 | 0 | 0 | 0 | 0 | | |
| | | Stem | 0 | 0 | 0 | 0 | 0 | 0 | 0 | 0 | | |
| | 2 | Leaf | 0 | 0 | 2 | 0 | 0 | 0 | 0 | 0 | 1 | |
| | | Petiole | 0 | 0 | 0 | 0 | 0 | 0 | 0 | 0 | 0 | |
| | | Stem | 0 | 0 | 0 | 0 | 0 | 0 | 0 | 0 | 0 | |
| HSR4720 | 1 | Leaf | 0 | 0 | 0 | 0 | 0 | 0 | 0 | 0 | | |
| | | Petiole | 0 | 0 | 0 | 0 | 0 | 0 | 0 | 0 | | |
| | | Stem | 0 | 0 | 0 | 0 | 0 | 0 | 0 | 0 | | |
| | 2 | Leaf | 0 | 0 | 0 | 0 | 0 | 0 | 0 | 0 | 0 | |
| | | Petiole | 0 | 0 | 0 | 0 | 0 | 0 | 0 | 0 | 0 | |
| | | Stem | 0 | 0 | 0 | 0 | 0 | 0 | 0 | 0 | 0 | |
| Magic Lantern | 1 | Leaf | 4 | 2 | 3 | 4 | 4 | 4 | | | | |
| | | Petiole | 2 | 3 | 2 | 2 | 3 | 3 | | | | |
| | | Stem | 1 | 2 | 1 | 3 | 2 | 3 | | | | |
| | 2 | Leaf | 4 | 4 | 4 | 5 | | | | | | |
| | | Petiole | 3 | 2 | 2 | 4 | | | | | | |
| | | Stem | 2 | 2 | 2 | 3 | | | | | | |
| HSR4707 | 2 | Leaf | 1 | 0 | 0 | 0 | 0 | 0 | 0 | 0 | 1 | |
| | | Petiole | 0 | 0 | 0 | 0 | 0 | 0 | 0 | 0 | 0 | |
| | | Stem | 0 | 0 | 0 | 0 | 0 | 0 | 0 | 0 | 0 | |
| Spartan | 1 | Leaf | 3 | 4 | 3 | | | | | | | |
| | | Petiole | 3 | 1 | 2 | | | | | | | |
| | | Stem | 3 | 2 | 2 | | | | | | | |
| | 2 | Leaf | 3 | 4 | 3 | | | | | | | |
| | | Petiole | 3 | 2 | 3 | | | | | | | |
| | | Stem | 2 | 3 | 3 | | | | | | | |
| HSR4709 | 1 | Leaf | 0 | 0 | 1 | 0 | 0 | 0 | 0 | 1 | 0 | 0 |
| | | Petiole | 0 | 0 | 0 | 0 | 0 | 0 | 0 | 0 | 0 | 0 |
| | | Stem | 0 | 0 | 0 | 0 | 0 | 0 | 0 | 0 | 0 | 0 |
| | 2 | Leaf | 0 | 0 | 1 | 0 | 0 | 0 | 0 | 2 | 0 | 0 |
| | | Petiole | 0 | 0 | 0 | 0 | 0 | 0 | 0 | 0 | 0 | 0 |
| | | Stem | 0 | 0 | 0 | 0 | 0 | 0 | 0 | 0 | 0 | 0 |
| HSR4711 | 1 | Leaf | 1 | 0 | 0 | 1 | 0 | 0 | 0 | 1 | 0 | 0 |
| | | Petiole | 0 | 0 | 0 | 0 | 0 | 0 | 0 | 0 | 0 | 0 |
| | | Stem | 0 | 0 | 0 | 0 | 0 | 0 | 0 | 0 | 0 | 0 |
| | 2 | Leaf | 0 | 1 | 0 | 0 | 0 | 0 | 1 | 0 | 0 | 1 |
| | | Petiole | 0 | 0 | 0 | 0 | 0 | 0 | 0 | 0 | 0 | 0 |
| | | Stem | 0 | 0 | 0 | 0 | 0 | 0 | 0 | 0 | 0 | 0 |
| Block II | | | | | | | | | | | | |
| HSR4709 | 1 | Leaf | 1 | 0 | 0 | 2 | 0 | 0 | 0 | 0 | 0 | 1 |
| | | Petiole | 0 | 0 | 0 | 0 | 0 | 0 | 0 | 0 | 0 | 0 |
| | | Stem | 0 | 0 | 0 | 0 | 0 | 0 | 0 | 0 | 0 | 0 |
| | 2 | Leaf | 0 | 0 | 1 | 0 | 1 | 0 | 0 | | | |
| | | Petiole | 0 | 0 | 0 | 0 | 0 | 0 | 0 | | | |
| | | Stem | 0 | 0 | 0 | 0 | 0 | 0 | 0 | | | |
| HSR4710 | 1 | Leaf | 1 | 0 | 0 | 0 | 0 | 0 | 1 | 0 | 0 | 0 |
| | | Petiole | 0 | 0 | 0 | 0 | 0 | 0 | 0 | 0 | 0 | 0 |
| | | Stem | 0 | 0 | 0 | 0 | 0 | 0 | 0 | 0 | 0 | 0 |
| HSR4710 | 2 | Leaf | 0 | 1 | 0 | 0 | 0 | 0 | 0 | 1 | | |
| | | Petiole | 0 | 0 | 0 | 0 | 0 | 0 | 0 | 0 | | |
| | | Stem | 0 | 0 | 0 | 0 | 0 | 0 | 0 | 0 | | |

TABLE 8-continued

| Trial Entries | Reps | Observed Organs | Mean Colonies/inch² Group (weeks after planting) | | | | | | | | | |
|---|---|---|---|---|---|---|---|---|---|---|---|---|
| | | | 1 | 2 | 3 | 4 | 5 | 6 | 7 | 8 | 9 | 10 |
| Magic Lantern | 1 | Leaf | 4 | 5 | 4 | | | | | | | |
| | | Petiole | 3 | 3 | 3 | | | | | | | |
| | | Stem | 2 | 3 | 3 | | | | | | | |
| | 2 | Leaf | 4 | 4 | 3 | | | | | | | |
| | | Petiole | 4 | 5 | 3 | | | | | | | |
| | | Stem | 3 | 3 | 4 | | | | | | | |
| HSR4707 | 1 | Leaf | 0 | 0 | 0 | 0 | 1 | 0 | 0 | 0 | 1 | |
| | | Petiole | 0 | 0 | 0 | 0 | 0 | 0 | 0 | 0 | 0 | |
| | | Stem | 0 | 0 | 0 | 0 | 0 | 0 | 0 | 0 | 0 | |
| | 2 | Leaf | 1 | 0 | 2 | 0 | 0 | 0 | 0 | 0 | 0 | |
| | | Petiole | 0 | 0 | 0 | 0 | 0 | 0 | 0 | 0 | 0 | |
| | | Stem | 0 | 0 | 0 | 0 | 0 | 0 | 0 | 0 | 0 | |
| Spartan | 1 | Leaf | 3 | 4 | 4 | | | | | | | |
| | | Petiole | 3 | 4 | 2 | | | | | | | |
| | | Stem | 2 | 3 | 3 | | | | | | | |
| | 2 | Leaf | 4 | 3 | 4 | 3 | | | | | | |
| | | Petiole | 3 | 2 | 3 | 2 | | | | | | |
| | | Stem | 2 | 3 | 2 | 3 | | | | | | |
| HSR4720 | 1 | Leaf | 0 | 0 | 0 | 0 | 0 | 0 | 0 | 0 | 0 | 0 |
| | | Petiole | 0 | 0 | 0 | 0 | 0 | 0 | 0 | 0 | 0 | 0 |
| | | Stem | 0 | 0 | 0 | 0 | 0 | 0 | 0 | 0 | 0 | 0 |
| | 2 | Leaf | 0 | 0 | 0 | 0 | 0 | 0 | 0 | 0 | 0 | 0 |
| | | Petiole | 0 | 0 | 0 | 0 | 0 | 0 | 0 | 0 | 0 | 0 |
| | | Stem | 0 | 0 | 0 | 0 | 0 | 0 | 0 | 0 | 0 | 0 |
| HSR4706 | 1 | Leaf | 0 | 1 | 1 | 0 | 0 | 0 | 0 | 0 | 0 | |
| | | Petiole | 0 | 0 | 0 | 0 | 0 | 0 | 0 | 0 | 0 | |
| | | Stem | 0 | 0 | 0 | 0 | 0 | 0 | 0 | 0 | 0 | |
| | 2 | Leaf | 0 | 1 | 1 | 0 | 0 | 0 | 0 | 0 | 0 | |
| | | Petiole | 0 | 0 | 0 | 0 | 0 | 0 | 0 | 0 | 0 | |
| | | Stem | 0 | 0 | 0 | 0 | 0 | 0 | 0 | 0 | 0 | |
| Merlin | 1 | Leaf | 3 | 4 | | | | | | | | |
| | | Petiole | 4 | 3 | | | | | | | | |
| | | Stem | 2 | 3 | | | | | | | | |
| Merlin | 2 | Leaf | 4 | 4 | | | | | | | | |
| | | Petiole | 3 | 3 | | | | | | | | |
| | | Stem | 4 | 3 | | | | | | | | |
| HSR4711 | 1 | Leaf | 0 | 1 | 0 | 0 | 0 | 0 | 0 | 2 | 0 | |
| | | Petiole | 0 | 0 | 0 | 0 | 0 | 0 | 0 | 0 | 0 | |
| | | Stem | 0 | 0 | 0 | 0 | 0 | 0 | 0 | 0 | 0 | |
| | 2 | Leaf | 0 | 1 | 0 | 0 | 1 | 0 | 0 | 0 | 0 | 1 |
| | | Petiole | 0 | 0 | 0 | 0 | 0 | 0 | 0 | 0 | 0 | 0 |
| | | Stem | 0 | 0 | 0 | 0 | 0 | 0 | 0 | 0 | 0 | 0 |

Statistical analysis using ANOVA of the data contained in Table 7 showed that the mean number of powdery mildew colonies on three parts (treatments) of plants were significantly different between the varieties containing the mutant allele Pm2 and the commercial varieties Merlin, Magic Lantern and Spartan (F=59.57, P<0.0001) (Table 7). For example, HSR4706 and HSR4707 both have a mean of 0.083 powdery mildew colonies, HSR4709 has a mean of about 0.069 powdery mildew colonies, HSR4710 has a mean of about 0.069 powdery mildew colonies, HSR4711 has a mean of about 0.042 powdery mildew colonies and HSR4720 has a mean of 0 powdery mildew colonies, while Magic Lantern has a mean of about 2.681 powdery mildew colonies, Merlin has a mean of about 3.306 powdery mildew colonies and Spartan has a mean of about 2.528 powdery mildew colonies. Using an F-test, when the number of powdery mildew colonies found per square inch per plant of individual varieties HSR4710, HSR4706, HSR4707, HSR4709 HSR4710, HSR4720 is compared individually with the number of powdery mildew colonies found on Merlin, Magic Lantern or Spartan, results indicate that each of the varieties of the present invention (HSR4710, HSR4706, HSR4707, HSR4709 HSR4710, HSR4720) have statistically significantly fewer powdery mildew colonies, (P<0.0001) than either Merlin, Magic Lantern or Spartan. The results indicate that the pumpkin varieties containing the mutant allele Pm2 of the present invention were at the same statistically significant level of powdery mildew resistance comparing that the commercial variety Merlin was significantly susceptible than Spartan and Magic Lantern. Overall, plants containing the Pm2 mutant allele of the present invention are significantly more resistant to powdery mildew than commercial varieties not containing the mutant allele Pm2 (Merlin, Magic Lantern and Spartan) ($\alpha$=0.05).

Table 9 shows the mean separation or paired comparison for colony counts for the pumpkin varieties containing the mutant allele Pm2 of the present invention with commercial pumpkin varieties Merlin, Magic Lantern and Spartan. "z" means with the same letter are not significantly different at 0.05 level. Magic Lantern, Spartan and Merlin are commercial pumpkin varieties used as comparisons, which do not carry the mutant PMR allele. "y" means the treatments consist of leaves, stems and petioles.

TABLE 9

| Varieties | Blocks | Replications | Treatments[y] | Mean[z] |
|---|---|---|---|---|
| Merlin | 2 | 2 | 3 | 3.306a |
| Magic Lantern | 2 | 2 | 3 | 2.681b |

TABLE 9-continued

| Varieties | Blocks | Replications | Treatments[y] | Mean[z] |
|---|---|---|---|---|
| Spartan | 2 | 2 | 3 | 2.528b |
| HSR4707 | 2 | 2 | 3 | 0.083c |
| HSR4706 | 2 | 2 | 3 | 0.083c |
| HSR4710 | 2 | 2 | 3 | 0.069c |
| HSR4709 | 2 | 2 | 3 | 0.069c |
| HSR4711 | 2 | 2 | 3 | 0.042c |
| HSR4720 | 2 | 2 | 3 | 0.000c |

2007 Trial for Powdery Mildew Resistance (Trial 6):

The data in Table 8 shows that the pumpkin varieties of the present invention, HSR4706, HSR4707, HSR4709 HSR4710, HSR4711 and HSR4720 grew vigorously during the entire season while the plants of commercial pumpkin varieties Merlin, Magic Lantern and Spartan continuously died out due to their susceptibility to the powdery mildew disease. Entries that do not contain a number (blank cells) mean that the plants died during the trial. When the plants were about 120 days old, the observed plants of Merlin, Spartan and Magic Lantern were about 80%, 70% and 60% died, respectively. It can be concluded that the pumpkin varieties of the present invention have a significant higher surviving rate than the commercial products under a high powdery mildew pressure.

An unexpected and significant difference of the mutant allele Pm2 versus Pm is that the lines or crosses carrying Pm2 always express Pm2 in a constant dominant manner at the seedling stage and at maturity. Tables 5 and 6 in the application show the phenotypic expression of the commercial varieties with Pm, Merlin, Magic Lantern and Spartan, analogue to that of Contin's 1978 experimental materials; susceptibility of which became higher so that many plants died from the powdery mildew infection as they were getting older. However, all crosses with the mutant allele Pm2 unexpectedly had a persistent powdery mildew resistance in the whole growing season and had a second fruit setting when all plants of commercial varieties with Pm were stopped from growing or dying from the disease. Similar results have been proven in many trials during the last four years. It was reported that Hollar PMR pumpkins Camaro, HSR4710 and HSR4721 had the lowest powdery mildew infection rate in the 2008 trial of Central Kentucky (Timothy Coolong and Kenneth Seebold, Evaluation of Powdery Mildew Tolerance in Pumpkin in Central Kentucky); the first two varieties, Hollar PMR pumpkins Camaro and HSR4710, also had the lowest amount of powdery mildew at 1% during the whole growing season (Elizabeth T. Maynard, Pumpkin Variety performance with and without treatment for powdery mildew in Northern Indiana, 2008). The fruit number was significantly higher for Hollar PMR pumpkins Camaro, HSR4710 and HSR4721 than the other tested varieties due to their PMR.

Fruit and Yield Trial Comparisons Under Powdery Mildew Pressure:

The yield data in Table 10 were taken from the survived plants in each plot across two replications and two blocks of a completely randomized-block-designed trial on Sep. 15, 2007. The plot yields were calculated based on marketable fruit number and their average weight after all rotten fruit were discarded. From the total number and the number of survived plants in all the plots, it shows that commercial pumpkin varieties Merlin, Magic Lantern and Spartan continually died-off during the growing season and lost about 50-80% of their yield at the end of the season due to the effects of powdery mildew. Column 1 in the table shows the variety, column two shows the replication number, column 3 shows the number of plants, column 4 shows the number of plants that survived, column 5 shows the fruit diameter in inches, column 6 shows the fruit height in inches, column 7 shows the total number of fruit, column 8 shows the number of rotten fruit, column 9 shows the number of marketable fruit, column 10 shows the average fruit weight in kilograms and column 11 shows the plot yield in kilograms.

TABLE 10

| Trial Entries (Variety) | Rep | # of Plants | # of Plants survived | Fruit Diameter (Inches) | Fruit Height (Inches) | Total fruit | Rotten fruit | Marketable fruit | Avg. Fruit wt (kg) | Plot yield (kg) |
|---|---|---|---|---|---|---|---|---|---|---|
| (Block I) | | | | | | | | | | |
| HSR4710 | 1 | 9 | 9 | 13.3 | 12.5 | 12 | 0 | 12 | 11.5 | 138 |
| | 2 | 8 | 7 | 13.5 | 12.25 | 12 | 1 | 11 | 12 | 132 |
| Merlin | 1 | 8 | 2 | 10.5 | 9.0 | 8 | 6 | 2 | 6.5 | 13 |
| | 2 | 10 | 3 | 11.0 | 10.5 | 14 | 8 | 6 | 7 | 42 |
| HSR4706 | 1 | 9 | 8 | 12.0 | 13.0 | 16 | 1 | 15 | 11.5 | 172.5 |
| | 2 | 12 | 10 | 11.5 | 12.5 | 25 | 2 | 23 | 11 | 253 |
| HSR4720 | 1 | 8 | 8 | 12.5 | 11.5 | 18 | 0 | 18 | 9.7 | 174.6 |
| | 2 | 10 | 9 | 12.0 | 11.0 | 20 | 3 | 17 | 9.5 | 161.5 |
| Magic Lantern | 1 | 13 | 6 | 13.5 | 11.0 | 18 | 9 | 9 | 10.5 | 94.5 |
| | 2 | 8 | 4 | 13.0 | 11.5 | 17 | 14 | 3 | 9.9 | 29.7 |
| HSR4721 | 1 | 8 | 8 | 11.0 | 9.5 | 22 | 0 | 22 | 6.9 | 151.8 |
| | 2 | 11 | 11 | 10.5 | 9.5 | 29 | 0 | 29 | 6.5 | 188.5 |
| HSR4707 | 1 | 10 | 9 | 10.0 | 11.5 | 21 | 0 | 21 | 8.6 | 180.6 |
| | 2 | 8 | 8 | 10.0 | 10.0 | 19 | 0 | 19 | 7.6 | 144.4 |
| HSR4722 | 1 | 7 | 7 | 11.5 | 10.5 | 18 | 1 | 17 | 8 | 136 |
| | 2 | 10 | 10 | 11.5 | 10.0 | 23 | 0 | 23 | 7.5 | 172.5 |
| Spartan | 1 | 11 | 3 | 9.5 | 9.0 | 20 | 13 | 7 | 6.5 | 45.5 |
| | 2 | 6 | 3 | 10.0 | 9.0 | 7 | 4 | 3 | 7 | 21 |
| HSR4709 | 1 | 10 | 10 | 13.5 | 13.0 | 18 | 0 | 18 | 12 | 216 |
| | 2 | 10 | 10 | 13.5 | 12.5 | 15 | 0 | 15 | 11.5 | 172.5 |
| HSR4711 | 1 | 13 | 12 | 12.0 | 11.25 | 20 | 2 | 18 | 8.6 | 154.8 |
| | 2 | 11 | 10 | 11.5 | 10.0 | 15 | 3 | 12 | 7.3 | 87.6 |
| (Block II) | | | | | | | | | | |
| HSR4709 | 1 | 7 | 7 | 12.5 | 13.5 | 13 | 2 | 11 | 11 | 121 |
| | 2 | 10 | 10 | 11.0 | 12.5 | 16 | 1 | 15 | 10 | 150 |

TABLE 10-continued

| Trial Entries (Variety) | Rep | # of Plants | # of Plants survived | Fruit Diameter (Inches) | Fruit Height (Inches) | Total fruit | Rotten fruit | Marketable fruit | Avg. Fruit wt (kg) | Plot yield (kg) |
|---|---|---|---|---|---|---|---|---|---|---|
| HSR4722 | 1 | 9 | 9 | 10.5 | 9.5 | 18 | 1 | 17 | 6.5 | 110.5 |
|  | 2 | 9 | 8 | 11.0 | 10.5 | 18 | 2 | 16 | 7 | 112 |
| HSR4710 | 1 | 11 | 11 | 10.5 | 10.0 | 21 | 0 | 21 | 6.3 | 132.3 |
|  | 2 | 12 | 11 | 12.0 | 9.0 | 17 | 0 | 17 | 9.5 | 161.5 |
| Magic Lantern | 1 | 10 | 3 | 13.0d | 12.5 | 20 | 16 | 4 | 10 | 40 |
|  | 2 | 11 | 3 | 12.5 | 10.5 | 19 | 16 | 3 | 8.5 | 25.5 |
| HSR4721 | 1 | 10 | 10 | 11.0 | 10.0 | 25 | 0 | 25 | 7 | 175 |
|  | 2 | 9 | 9 | 10.5 | 10.0 | 22 | 0 | 22 | 7 | 154 |
| HSR4707 | 1 | 9 | 9 | 12.0 | 11.5 | 17 | 0 | 17 | 11 | 187 |
|  | 2 | 10 | 9 | 10.5 | 10.0 | 24 | 2 | 22 | 6.5 | 143 |
| Spartan | 1 | 9 | 4 | 10.5 | 9.0 | 17 | 12 | 5 | 6.7 | 33.5 |
|  | 2 | 9 | 3 | 11.0 | 9.5 | 13 | 7 | 6 | 7 | 42 |
| HSR4720 | 1 | 12 | 12 | 9.0 | 10.5 | 25 | 0 | 25 | 7.5 | 187.5 |
|  | 2 | 10 | 10 | 11.0 | 12.0 | 23 | 0 | 23 | 10.7 | 246.1 |
| HSR4706 | 1 | 10 | 9 | 12.0 | 12.5 | 21 | 0 | 21 | 8.8 | 184.8 |
|  | 2 | 9 | 9 | 11.5 | 12.0 | 20 | 0 | 20 | 8 | 160 |
| Merlin | 1 | 8 | 2 | 10.5 | 9.0 | 12 | 10 | 2 | 6.8 | 13.6 |
|  | 2 | 12 | 2 | 10.0 | 8.5 | 19 | 16 | 3 | 6.5 | 19.5 |
| HSR4711 | 1 | 10 | 10 | 10.5 | 12.0 | 16 | 0 | 16 | 9.5 | 152 |
|  | 2 | 9 | 9 | 9.0 | 12.0 | 14 | 1 | 13 | 9 | 117 |

Table 11 below shows the mean separation or multiple paired comparison for yield for the pumpkin varieties containing the mutant allele Pm2 of the present invention with commercial pumpkin varieties Merlin, Magic Lantern and Spartan. "z" means with the same letter are not significantly different at 0.05 level. Magic Lantern, Spartan and Merlin are commercial pumpkin varieties used as comparisons, which do not carry the mutant Pm2 allele.

By multiple paired comparisons of yields among pumpkins containing the mutant allele Pm2 of the present invention and commercial pumpkin varieties Merlin, Magic Lantern and Spartan, it was found that the yields of the pumpkins containing the Pm2 mutant allele of the present invention were statistically significantly higher than the commercial pumpkin varieties Magic, Lantern and Spartan and of Merlin at 0.05 level. Although pumpkins of the present invention HSR4706, HSR4720 have a significantly higher yield than HSR4721, HSR4709 and 4707 which have a significantly higher yield than HSR4710, HSR4722 and HSR4711, the commercial varieties Magic Lantern, Spartan and Merlin are about 70% lower in their yields due to the powdery mildew infection.

TABLE 11

| Varieties | Blocks | Replications | Mean (Kg)$^z$ |
|---|---|---|---|
| HSR4706 | 2 | 2 | 192.47a |
| HSR4720 | 2 | 2 | 192.43a |
| HSR4721 | 2 | 2 | 167.32ab |
| HSR4709 | 2 | 2 | 164.87ab |
| HSR4707 | 2 | 2 | 163.75ab |
| HSR4710 | 2 | 2 | 140.95b |
| HSR4722 | 2 | 2 | 132.75b |
| HSR4711 | 2 | 2 | 127.85b |
| Magic Lantern | 2 | 2 | 47.42c |
| Spartan | 2 | 2 | 35.50c |
| Merlin | 2 | 2 | 22.02c |

Example 5

Describing the Features of the Invention

Inbred pumpkin HSPMR7B1 has the following morphologic and other characteristics (based primarily on data collected at Rocky Ford, Colo.).

HSPMR7B1 Variety Description

Genus: *Cucurbita*
Species: *Pepo*
Type: Pumpkin
Cotyledons:
Length: 8.0 cm
Width: 4.5 cm
Veining: Obscure
Color: Medium green
Plant: Reduced vine
Prickly
Leaves:
Shape: Heart-shaped; shallow lobe
Margin: Dentate
Length: 40.0 cm
Width: 34.0 cm
Upper-surface: Bristled
Ventral surface: Bristled
Color: Medium green; not blotched
Petiole:
Length: 41.0 cm
Flower (staminate):
Sepals:
   Length: 3.0 cm
   Width: 0.15 cm
Pedicel:
   Length: 30.0 cm
Color: Bright yellow
Fruit (at market maturity):
Height: 30.0 cm
Width: 31.0 cm
Apex: Flat-rounded
Base: Flat-rounded
Ribs: None
Rib furrows: Inconspicuous
Fruit surface: Smooth
Warts: None
Blossom scar button: Slightly depressed
Rind: Medium hard
   Thickness: 0.2 cm
   Color pattern: Regular; orange Flesh:
  Thickness:
    Blossom end: 2.7 cm
    Medial: 3.0 cm
    Stem end: 3.5 cm
  Texture: Stringy; firm; moist
  Color: Yellow-orange
Seed cavity (sectioned apex to base):
  Length: 24.0 cm
  Width: 25.0 cm
  Location: Conforms to fruit shape
  Placental tissue: Abundant
  Center core: Inconspicuous
Fruit stalks:
  Length: 11.0 cm
  Diameter: 3.5 cm
  Texture: Medium hard
  Furrows: Medium deep
  Surface: Slightly spiny
  Attachment end: Expanded
  Detaches: With difficulty
  Color: Medium green
Seeds:
Length: 2.0 cm
Width: 1.1 cm
Thickness: 0.2 cm
Face surface: Smooth
Color: Cream
Margin: Wedge-like
Separation from pulp: Easy
Weight of 100 seeds: 18.0 gm
Powdery mildew resistance rating: Resistant Example 6

Determining Genetic Similarity Between the Mutant Allele Pm2 of the Present Invention and that of Three Commercially Available Pumpkin Varieties The genetic similarity between the mutant allele Pm2 of the present invention and that of three commercially available pumpkin varieties was determined. DNA-based SSR, ISSR and RAPD markers were used to compare the genetic relationships of four pumpkin hybrids in April of 2006. The four pumpkin hybrids were Merlin, Spartan, Frosty, and HSR4709. Merlin and Spartan are commercially available pumpkin hybrids that display a lower level of powdery mildew resistance, while Frosty is a commercially available pumpkin hybrid which is powdery mildew susceptible and was used as a control. HSR4709 is a pumpkin hybrid containing the mutant allele Pm2 of the present invention. Seeds of the four hybrids were planted and germinated in a greenhouse for the purpose of leaf sampling for DNA extraction. Approximately five weeks post germination date about 40 young leaves from each variety were pooled and placed into sterile 1.5 ml microcentrifuge tubes. Tubes containing the leaf samples were freeze-dried overnight with caps open. Genomic DNA was isolated from each entry using a modified CTAB method, quantified by a DNA Flourometer (HOEFER DyNA Quant 200, Amersham Pharmacia Biotech, USA) and adjusted to 25 ng/µl in sterile TE buffer.

Three different sets of oligonucleotide primers were used to amplify genomic DNA of each entry with minor modifications. All PCR amplifications were carried out in duplicate for accuracy and amplification consistency. Microsatellite markers designed for *C. melo* (Chiba et al. 2003, *Breeding Science* 53:21-27), Inter-simple-sequence-repeat (ISSR) primers of 15-23 nucleotides in length (UBC set #9, Biotechnology Laboratory, University of British Columbia, Vancouver, Canada) and Random Amplified Polymorphic DNA Primers (RAPD) of 10 bases in length (Set #9, Genemed Synthesis, Inc. South San Francisco, Calif., USA) were applied for DNA amplification. Microsatellite (SSR) and ISSRs were amplified as described by Chiba et al. (2003) using 160 mM $(NH_4)_2SO_4$, 670 mM Tris-HCl (pH 8.8 at 25° C.), 0.1% Tween-20, 2.0 mM $MgCl_2$, 2.5 mM dNTP, 4 µM primer, 25 ng of genomic DNA per 10 µl of reaction volume and 1.0 U of Biolase DNA Polymerase (Bioline USA Inc., Kenilworth, N.J., USA) for 1 cycle denaturation at 94° C. for 3 minutes, followed by 35 cycles at 94° C. for 60 seconds, 45-60° C. for 60 sec, and 72° C. for 1 minute, and a 5 minute final extension at 72° C. DNA amplification by 10-mer oligonucleotide primers was performed exactly as described above except at an annealing temperature of 35° C. for a total of 40 PCR cycles.

All generated amplicons were separated on 6% polyacrylamide gels. Gels were stained with silver staining method and scored for presence and absence of bands. A locus was considered to be polymorphic if the band was present in one entry and not in the other. The assumption was made that the scored bands were homozygous. Slight distortion of genetic distance could exist by over-estimating genetic similarity with the possibility of the presence of heterozygous bands, which is of greater concern in backcross breeding program than in a database. Monomorphic bands were scored but were not included in any calculations. All of the genotypic data for each entry was scored as a dominant marker.

Coefficients for genetic similarity (GS) between pairs of cultivars were calculated according to Nei and Li (1979):

$$GS=2N_{ij}/(N_i+N_j)$$

Where GS equals the similarity coefficient between cultivars i and j, $N_{ij}$ equals the number of common bands present in both i and j cultivars, and $N_i$ and $N_j$ reflect the total of bands detected in cultivars i and j, respectively. GS assessment may attain any value between 0 and 1, where 0 means "no bands in common" and 1 means "patterns are identical." Consequently, identity of two cultivars will give rise to a GS value of 1, while totally unrelated cultivars will give rise to a GS value of zero. The larger the GS value the more similarities between the entries. It is important to state that a DNA fingerprint of a particular sample is rarely informative on its own. Therefore, as a comparative analysis, the DNA patterns of different samples have to be compared to each other in order to estimate the degree of relatedness. The generated GS values are not absolute and often yield only approximations, becoming intricate to interpret. Such values may be relative to the variability within and between the genetic populations, methodological parameters such DNA marker systems and the statistical methods used for the analysis. For example, a GS value of 0.900 may be interpreted as genetically being the same variety in one species, such as in a highly heterogeneous and obligate open-pollinating crop with an elevated inherent variability within a given variety. In other species, such as in highly homozygous inbred and self-pollinating lines or varieties, a high GS value of 0.980 or 1.00 may be required to demonstrate genetic identity.

Three types of DNA markers were employed in this study, melon microsatellites (SSR), ISSR and RAPD. The genomic DNA of each entry was analyzed in duplicates using 14, 44 and 36 melon microsatellites (SSR), ISSR and RAPD primers, respectively. Repeatable amplifications were produced for most of the primers. In total, the primer combinations yielded 2372 amplification products of which 563 (24%)

were polymorphic. The produced and scored polymorphic bands were in general well spaced with easily scoreable bands. The amplification of each entry was carried out in duplicate and no major band discrepancies between reps were noted. Therefore, the scored and highly visible banding pattern under the described amplification conditions of this experiment is considered as being highly repeatable and reliable.

The presence or absence of DNA amplification fingerprint fragments in the pumpkin genotypes considered gave rise to a matrix used to calculate the coefficient of genetic similarity index (GSI) among the four pumpkin lines. The index values indicate the degree of genetic relationship of one entry with another. The index values in Table 10 ranged from 0.324 for hybrids Merlin and HSR4709 to 0.592 for hybrids Spartan and Merlin. As noted the degree of relatedness between the hybrids is described as the genetic similarity index value. For example, the Nei and Li (N&L) genetic similarity index for hybrids Merlin and HSR4709 is 0.324. If this is a truly random sample of DNA markers, which it is, then 95% (i.e. 95% confidence) of random 94 genetic DNA polymorphisms will be between 0.270 and 0.38 confidence limits. In Table 11, LCL means the lower confidence limit at 95% probability level and UCL means the upper confidence limit at 95% probability level.

The results in Table 10 and Table 11 demonstrated that the genetic relationship (GS=0.503) of the new pumpkin HSR4709, which contains the mutant allele Pm2 of the present invention, and PMS pumpkin Frosty were much closer than either of the commercial variety Merlin (GS=0.324) or Spartan (GS=0.362). This shows that the powdery mildew resistance displayed by HSR4709 containing the mutant allele Pm2 of the present invention was derived from a different genetic source from that of either Merlin or Spartan.

TABLE 12

|  | Merlin | HSR4709 | Frosty | Spartan |
|---|---|---|---|---|
| Merlin | 1.000 | 0.324 | 0.370 | 0.592 |
| HSR4709 | 0.324 | 1.000 | 0.503 | 0.362 |
| Frosty | 0.370 | 0.503 | 1.000 | 0.467 |
| Spartan | 0.592 | 0.362 | 0.467 | 1.000 |

TABLE 13

|  |  | LCL | UCL |
|---|---|---|---|
| Merlin | HSR4709 | 0.27 | 0.38 |
| Merlin | Frosty | 0.31 | 0.43 |
| Merlin | Spartan | 0.53 | 0.65 |
| HSR4709 | Frosty | 0.45 | 0.56 |
| HSR4709 | Spartan | 0.31 | 0.42 |
| Frosty | Spartan | 0.41 | 0.53 |

Table 12 shows the mean separation or paired comparison for colony counts for the pumpkin varieties containing the mutant allele Pm2 of the present invention with commercial pumpkin varieties Merlin, Magic Lantern and Spartan. "z" means with the same letter are not significantly different at 0.05 level. Magic Lantern, Spartan and Merlin are commercial pumpkin varieties used as comparisons, which do not carry the mutant Pm2 allele. "y" means the treatments consist of leaves, stems and petioles.

Further Embodiments of the Invention

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes." Over the last fifteen to twenty years several methods for producing transgenic plants have been developed and the present invention, in particular embodiments, also relates to transformed versions of the claimed variety or line.

Plant transformation involves the construction of an expression vector which will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid and can be used alone or in combination with other plasmids to provide transformed *C. pepo* plants using transformation methods as described below to incorporate transgenes into the genetic material of the *C. pepo* plant(s).

Expression Vectors for *C. Pepo* Transformation: Marker Genes

Expression vectors include at least one genetic marker operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene which, when under the control of plant regulatory signals, confers resistance to kanamycin. Fraley et al., *Proc. Natl. Acad. Sci. USA,* 80:4803 (1983). Another commonly used selectable marker gene is the hygromycin phosphotransferase gene which confers resistance to the antibiotic hygromycin. Vanden Elzen et al., *Plant Mol. Biol.,* 5:299 (1985).

Additional selectable marker genes of bacterial origin that confer resistance to antibiotics include gentamycin acetyl transferase, streptomycin phosphotransferase and aminoglycoside-3'-adenyl transferase, the bleomycin resistance determinant (Hayford et al., *Plant Physiol.* 86:1216 (1988), Jones et al., *Mol. Gen. Genet.,* 210:86 (1987), Svab et al., *Plant Mol. Biol.* 14:197 (1990), Hille et al., *Plant Mol. Biol.* 7:171 (1986)). Other selectable marker genes confer resistance to herbicides such as glyphosate, glufosinate or bromoxynil (Comai et al., *Nature* 317:741-744 (1985), Gordon-Kamm et al., *Plant Cell* 2:603-618 (1990) and Stalker et al., *Science* 242:419-423 (1988)).

Selectable marker genes for plant transformation not of bacterial origin include, for example, mouse dihydrofolate reductase, plant 5-enolpyruvylshikimate-3-phosphate synthase and plant acetolactate synthase (Eichholtz et al., *Somatic Cell Mol. Genet.* 13:67 (1987), Shah et al., *Science* 233:478 (1986), Charest et al., *Plant Cell Rep.* 8:643 (1990)).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase (Jefferson, R. A., *Plant Mol. Biol. Rep.* 5:387 (1987), Teeri et al., *EMBO J.* 8:343 (1989), Koncz et al., *Proc. Natl. Acad. Sci. USA* 84:131 (1987), DeBlock et al., *EMBO J.* 3:1681 (1984)).

In vivo methods for visualizing GUS activity that do not require destruction of plant tissue are available (Molecular Probes publication 2908, IMAGENE GREEN, pp. 1-4 (1993) and Naleway et al., *J. Cell Biol.* 115:151a (1991)). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells (Chalfie et al., *Science* 263: 802 (1994)). GFP and mutants of GFP may be used as screenable markers.

Expression Vectors for *C. Pepo* Transformation: Promoters

Genes included in expression vectors must be driven by a nucleotide sequence comprising a regulatory element, for example, a promoter. Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in a certain tissue are referred to as "tissue-specific." A "cell-type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter that is active under most environmental conditions.

A. Inducible Promoters:

An inducible promoter is operably linked to a gene for expression in *C. pepo*. Optionally, the inducible promoter is operably linked to a nucleotide sequence encoding a signal sequence which is operably linked to a gene for expression in *C. pepo*. With an inducible promoter the rate of transcription increases in response to an inducing agent.

Any inducible promoter can be used in the instant invention. See Ward et al., *Plant Mol. Biol.* 22:361-366 (1993). Exemplary inducible promoters include, but are not limited to, that from the ACEI system which responds to copper (Melt et al., *Proc. Natl. Acad. Sci. USA* 90:4567-4571 (1993)); In2 gene from maize which responds to benzenesulfonamide herbicide safeners (Hershey et al., *Mol. Gen Genetics* 227:229-237 (1991) and Gatz et al., *Mol. Gen. Genetics* 243:32-38 (1994)) or Tet repressor from Tn10 (Gatz et al., *Mol. Gen. Genetics* 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena et al., *Proc. Natl. Acad. Sci. USA* 88:0421 (1991)).

B. Constitutive Promoters:

A constitutive promoter is operably linked to a gene for expression in *C. pepo* or the constitutive promoter is operably linked to a nucleotide sequence encoding a signal sequence which is operably linked to a gene for expression in *C. pepo*.

Many different constitutive promoters can be utilized in the instant invention. Exemplary constitutive promoters include, but are not limited to, the promoters from plant viruses such as the 35S promoter from CaMV (Odell et al., *Nature* 313:810-812 (1985)) and the promoters from such genes as rice actin (McElroy et al., *Plant Cell* 2: 163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)) and maize H3 histone (Lepetit et al., *Mol. Gen. Genetics* 231:276-285 (1992) and Atanassova et al., *Plant Journal* 2 (3): 291-300 (1992)). The ALS promoter, Xba1/Nco1 fragment 5' to the *Brassica napus* ALS3 structural gene (or a nucleotide sequence similarity to said Xba1/Nco1 fragment), represents a particularly useful constitutive promoter. See PCT publication number WO 96/30530.

C. Tissue-Specific or Tissue-Preferred Promoters:

A tissue-specific promoter is operably linked to a gene for expression in *C. pepo*. Optionally, the tissue-specific promoter is operably linked to a nucleotide sequence encoding a signal sequence which is operably linked to a gene for expression in *C. pepo*. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter such as that from the phaseolin gene (Murai et al., *Science* 23:476-482 (1983) and Sengupta-Gopalan et al., *Proc. Natl. Acad. Sci. USA* 82:3320-3324 (1985)); a leaf-specific and light-induced promoter such as that from cab or rubisco (Simpson et al., *EMBO J.* 4(11): 2723-2729 (1985) and Timko et al., *Nature* 318:579-582 (1985)); an anther-specific promoter such as that from LAT52 (Twell et al., *Mol. Gen. Genetics* 217:240-245 (1989)); a pollen-specific promoter such as that from Zm13 (Guerrero et al., *Mol. Gen. Genetics* 244:161-168 (1993)) or a microspore-preferred promoter such as that from apg (Twell et al., *Sex. Plant Reprod.* 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine during protein synthesis and processing where the encoded protein is ultimately compartmentalized.

The presence of a signal sequence directs a polypeptide to either an intracellular organelle or subcellular compartment or for secretion to the apoplast. Many signal sequences are known in the art. See, for example, Becker et al., *Plant Mol. Biol.* 20:49 (1992); Close, P. S., Master's Thesis, Iowa State University (1993); Knox, C., et al., *Plant Mol. Biol.* 9:3-17 (1987); Lerner et al., *Plant Physiol.* 91:124-129 (1989); Frontes et al., *Plant Cell* 3:483-496 (1991); Matsuoka et al., *Proc. Natl. Acad. Sci.* 88:834 (1991); Gould et al., *J. Cell. Biol.* 108:1657 (1989); Creissen et al., *Plant J.* 2:129 (1991); Kalderon, et al., *Cell* 39:499-509 (1984); Steifel, et al., *Plant Cell* 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92-6 (1981).

According to a preferred embodiment, the transgenic plant provided for commercial production of foreign protein is a *C. pepo* plant. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, *Methods in Plant Molecular Biology and Biotechnology*, CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

A. Genes that Confer Resistance to Pests or Disease and that Encode:

1. Plant disease resistance genes. Plant defenses are often activated by specific interaction between the product of a disease resistance gene (R) in the plant and the product of a corresponding avirulence (Avr) gene in the pathogen. A plant variety can be transformed with one or more cloned resistance genes to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. tomato encodes a protein kinase); Mindrinos et al. *Cell* 78:1089 (1994) (*Arabidopsis* RSP2 gene for resistance to *Pseudomonas syringae*).

2. A gene conferring resistance to a pest, such as soybean cyst nematode. See e.g., PCT Publication Number WO 96/30517; PCT Publication Number WO 93/19181.

3. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Numbers 40098, 67136, 31995, and 31998.

4. A lectin. See, for example, Van Damme et al., *Plant Molec. Biol.* 24:25 (1994), who disclose the nucleotide sequences of several *Clivia miniata* mannose-binding lectin genes.

5. A vitamin-binding protein such as avidin. See PCT Application Number U.S. 93/06487 which teaches the use of avidin and avidin homologues as larvicides against insect pests.

6. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* α-amylase inhibitor) and U.S. Pat. No. 5,494,813 (Hepher and Atkinson, issued Feb. 27, 1996).

7. An insect-specific hormone or pheromone such as an ecdysteroid or juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

8. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*). See also U.S. Pat. No. 5,266,317 to Tomalski et al., which discloses genes encoding insect-specific, paralytic neurotoxins.

9. An insect-specific venom produced in nature by a snake, a wasp, etc. For example, see Pang et al., *Gene* 116:165 (1992), for disclosure of heterologous expression in plants of a gene coding for a scorpion insectotoxic peptide.

10. An enzyme responsible for a hyperaccumulation of a monoterpene, a sesquiterpene, a steroid, hydroxamic acid, a phenylpropanoid derivative or another non-protein molecule with insecticidal activity.

11. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT Publication WO 93/02197 (Scott et al.), which discloses the nucleotide sequence of a callase gene. DNA molecules which contain chitinase-encoding sequences can be obtained, for example, from the ATCC under Accession Numbers 39637 and 67152. See also Kramer et al., *Insect Biochem. Molec. Biol.* 23:691 (1993), who teach the nucleotide sequence of a cDNA encoding tobacco hornworm chitinase, and Kawalleck et al., *Plant Molec. Biol.* 21:673 (1993), who provide the nucleotide sequence of the parsley ubi4-2 polyubiquitin gene.

12. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

13. A hydrophobic moment peptide. See PCT Publication WO 95/16776, which discloses peptide derivatives of tachyplesin which inhibit fungal plant pathogens, and PCT Publication WO 95/18855 which teaches synthetic antimicrobial peptides that confer disease resistance.

14. A membrane permease, a channel former or a channel blocker. For example, see the disclosure of Jaynes et al., *Plant Sci* 89:43 (1993), of heterologous expression of a cecropin-β lytic peptide analog to render transgenic tobacco plants resistant to *Pseudomonas solanacearum*.

15. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28:451 (1990). Coat protein-mediated resistance has been conferred upon transformed plants against alfalfa mosaic virus, cucumber mosaic virus and tobacco mosaic virus.

16. An insect-specific antibody or an immunotoxin derived therefrom. Thus, an antibody targeted to a critical metabolic function in the insect gut would inactivate an affected enzyme, killing the insect. See Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

17. A virus-specific antibody. See, for example, Tavladoraki et al., *Nature* 366:469 (1993), who show that transgenic plants expressing recombinant antibody genes are protected from virus attack.

18. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

19. A developmental-arrestive protein produced in nature by a plant. For example, Logemann et al., *Bio/Technology* 10:305 (1992), have shown that transgenic plants expressing the barley ribosome-inactivating gene have an increased resistance to fungal disease.

20. Genes involved in the Systemic Acquired Resistance (SAR) Response and/or the pathogenesis-related genes. Briggs, S., *Current Biology*, 5(2) (1995).

21. Antifungal genes. See Cornelissen and Melchers, *Plant Physiol.*, 101:709-712 (1993); Parijs et al., *Planta* 183:258-264 (1991) and Bushnell et al., *Can. J. of Plant Path.* 20(2):137-149 (1998).

22. Genes that confer resistance to *Phytophthora* root rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker et al., *Phytophthora* Root Rot Resistance Gene Mapping in Soybean, Plant Genome IV Conference, San Diego, Calif. (1995).

B. Genes that Confer Resistance to an Herbicide, for Example:

1. An herbicide that inhibits the growing point or meristem, such as an imidazolinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

2. Glyphosate (resistance conferred by mutant 5-enolpyruvlshikimate-3-phosphate synthase (EPSPS) and aroA genes, respectively) and other phosphono compounds such as glufosinate (phosphinothricin acetyl transferase (PAT) and *Streptomyces hygroscopicus* PAT bar genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPS which can confer glyphosate resistance. A DNA molecule encoding a mutant aroA gene can be obtained under ATCC Accession Number 39256, and the nucleotide sequence of the mutant gene is disclosed in U.S. Pat. No. 4,769,061 to Comai. European Patent Application Number 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European Application Number 0 242 246 to Leemans et al. DeGreef et al., *Bio/Technology* 7:61 (1989) describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop are the Acc1-S1, Acc1-S2, and Acc2-S3 genes described by Marshall et al., *Theor. Appl. Genet.* 83:435 (1992).

3. An herbicide that inhibits photosynthesis, such as a triazine (psbA and gs+ genes) and a benzonitrile (nitrilase gene). Przibila et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC Accession Numbers 53435, 67441, and 67442. Cloning and expression of DNA coding for a glutathione S-transferase is described by Hayes et al., *Biochem. J.* 285:173 (1992).

4. Acetohydroxy acid synthase, which has been found to make plants that express this enzyme resistant to multiple types of herbicides, has been introduced into a variety of plants. See Hattori et al., *Mol. Gen. Genet.* 246:419, 1995. Other genes that confer tolerance to herbicides include a gene encoding a chimeric protein of rat cytochrome P4507A1 and yeast NADPH-cytochrome P450 oxidoreductase (Shiota et al., *Plant Physiol.*, 106:17, 1994), genes for glutathione reductase and superoxide dismutase (Aono et al., *Plant Cell Physiol.* 36:1687, 1995), and genes for various phosphotransferases (Datta et al., *Plant Mol. Biol.* 20:619, 1992).

5. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,837; 5,767,373; and PCT Publication WO 01/12825.

C. Genes that Confer or Contribute to a Value-Added Trait, Such as:

1. Modified fatty acid metabolism, for example, by transforming a plant with an antisense gene of stearyl-ACP desaturase to increase stearic acid content of the plant. See Knultzon et al., *Proc. Natl. Acad. Sci. USA* 89:2625 (1992).

2. Decreased phytate content—1) Introduction of a phytase-encoding gene enhances breakdown of phytate, adding more free phosphate to the transformed plant. For example, see Van Hartingsveldt et al., *Gene* 127:87 (1993), for a disclosure of the nucleotide sequence of an *Aspergillus niger* phytase gene. 2) A gene could be introduced that reduced phytate content. This could be accomplished by cloning and then reintroducing DNA associated with the single allele which is responsible for maize mutants characterized by low levels of phytic acid. See Raboy et al., *Maydica* 35:383 (1990).

3. Modified carbohydrate composition effected, for example, by transforming plants with a gene coding for an enzyme that alters the branching pattern of starch. See Shiroza et al., *J. Bacteriol.* 170:810 (1988) (nucleotide sequence of *Streptococcus mutants* fructosyltransferase gene), Steinmetz et al., *Mol. Gen. Genet.* 20:220 (1985) (nucleotide sequence of *Bacillus subtilis* levansucrase gene), Pen et al., *Bio/Technology* 10:292 (1992) (production of transgenic plants that express *Bacillus licheniformis* α-amylase), Elliot et al., *Plant Molec. Biol.* 21:515 (1993) (nucleotide sequences of tomato invertase genes), Søgaard et al., *J. Biol. Chem.* 268:22480 (1993) (site-directed mutagenesis of barley α-amylase gene), and Fisher et al., *Plant Physiol.* 102:1045 (1993) (maize endosperm starch branching enzyme II).

4. Elevated oleic acid via FAD-2 gene modification and/or decreased linolenic acid via FAD-3 gene modification. See U.S. Pat. Nos. 6,063,947; 6,323,392; and PCT Publication WO 93/11245.

D. Genes that Control Male Sterility:

1. Introduction of a deacetylase gene under the control of a tapetum-specific promoter and with the application of the chemical N-Ac-PPT. See PCT Publication WO 01/29237.

2. Introduction of various stamen-specific promoters. See PCT Publications WO 92/13956 and WO 92/13957.

3. Introduction of the barnase and the barstar genes. See Paul et al., *Plant Mol. Biol.* 19:611-622, 1992).

Methods for *C. Pepo* Transformation

Numerous methods for plant transformation have been developed including biological and physical plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc. Boca Raton, 1993) pages 67-88. In addition, expression vectors and in-vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

A. *Agrobacterium*-Mediated Transformation

One method for introducing an expression vector into plants is based on the natural transformation system of *Agrobacterium*. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of *Agrobacterium* vector systems and methods for *Agrobacterium*-mediated gene transfer are provided by Gruber et al., supra, Miki et al., supra and Moloney et al., *Plant Cell Reports* 8:238 (1989). See also, U.S. Pat. No. 5,563,055 (Townsend and Thomas), issued Oct. 8, 1996.

B. Direct Gene Transfer

Several methods of plant transformation, collectively referred to as direct gene transfer, have been developed as an alternative to *Agrobacterium*-mediated transformation. A generally applicable method of plant transformation is microprojectile-mediated transformation where DNA is carried on the surface of microprojectiles measuring 1 μm to 4 μm. The expression vector is introduced into plant tissues with a biolistic device that accelerates the microprojectiles to speeds of 300 m/s to 600 m/s which is sufficient to penetrate plant cell walls and membranes. Sanford et al., *Part. Sci. Technol.* 5:27 (1987); Sanford, J. C., *Trends Biotech.* 6:299 (1988); Klein et al., *Bio/Tech.* 6:559-563 (1988); Sanford, J. C. *Physiol Plant* 7:206 (1990); Klein et al., *Biotechnology* 10:268 (1992). See also U.S. Pat. No. 5,015,580 (Christou, et al.), issued May 14, 1991 and U.S. Pat. No. 5,322,783 (Tomes, et al.), issued Jun. 21, 1994.

Another method for physical delivery of DNA to plants is sonication of target cells. Zhang et al., *Bio/Technology* 9:996 (1991). Alternatively, liposome and spheroplast fusion have been used to introduce expression vectors into plants. Deshayes et al., *EMBO J.,* 4:2731 (1985); Christou et al., *Proc Natl. Acad. Sci. USA* 84:3962 (1987). Direct uptake of DNA into protoplasts using $CaCl_2$ precipitation, polyvinyl alcohol or poly-L-ornithine have also been reported. Hain et al., *Mol. Gen. Genet.* 199:161 (1985) and Draper et al., *Plant Cell Physiol.* 23:451 (1982). Electroporation of protoplasts and whole cells and tissues have also been described (Donn et al., In Abstracts of VIIth International Congress on Plant Cell and Tissue Culture IAPTC, A2-38, p 53 (1990); D'Halluin et al., *Plant Cell* 4:1495-1505 (1992) and Spencer et al., *Plant Mol. Biol.* 24:51-61 (1994)).

Following transformation of *C. pepo* target tissues, expression of the above-described selectable marker genes allows for preferential selection of transformed cells, tissues and/or plants, using regeneration and selection methods well known in the art.

The foregoing methods for transformation would typically be used for producing a transgenic variety. The transgenic variety could then be crossed with another (non-transformed or transformed) variety in order to produce a new transgenic variety. Alternatively, a genetic trait that has been engineered into a particular *C. pepo* line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties that do not contain that gene. As used herein, "crossing" can refer to a simple X by Y cross or the process of backcrossing depending on the context.

Gene Conversions

When the term "*C. pepo* plant" is used in the context of the present invention, this also includes any single gene conversions of that variety. The term single gene converted or gene converted plant as used herein refers to those *C. pepo* plants which are developed by a plant breeding technique called backcrossing wherein essentially all of the desired morphological and physiological characteristics of a variety are recovered in addition to the single gene transferred into the variety via the backcrossing technique. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8 or more times to the recurrent parent. The parental *C. pepo* plant that contributes the gene for the desired characteristic is termed the nonrecurrent or donor parent. This terminology refers to the fact that the nonrecurrent parent is used one time in the backcross protocol and therefore does not recur. The parental *C. pepo* plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original variety of interest (recurrent parent) is crossed to a second variety (nonrecurrent parent) that carries the single gene or genes of interest to be transferred. The resulting progeny from this cross are then crossed again to the recurrent parent and the process is repeated until a *C. pepo* plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological, constitution of the original variety. The choice of the particular nonrecurrent parent will depend on the purpose of the backcross; one of the major purposes is to add some agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single or multiple gene traits have been identified that are not regularly selected for in the development of a new variety but that can be improved by backcrossing techniques. Single gene traits may or may not be transgenic; examples of these traits include but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Several of these single gene traits are described in U.S. Pat. Nos. 5,959,185; 5,973,234 and 5,977,445; the disclosures of which are specifically hereby incorporated by reference.

Tissue Culture

Further reproduction of a variety can occur by tissue culture and regeneration. Tissue culture of various tissues of *C. pepo* and regeneration of plants therefrom is well known and widely published. For example, reference may be had to Jelaska, S. et al., *Physiol. Plant.* 64(2):237-242 (1985) and Krsnik-Rasol, M., *Int. J. Dev. Biol.* 35(3):259-263 (1991). Thus, another aspect of this invention is to provide cells which upon growth and differentiation produce *C. pepo* plants having the mutant allele Pm2.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, leaves, stems, roots, root tips, anthers, pistils and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

Additional Breeding Methods

This invention also is directed to methods for producing a *C. pepo* plant by crossing a first parent *C. pepo* plant with a second parent *C. pepo* plant wherein the first or second parent *C. pepo* plant is a *C. pepo* plant comprising the mutant allele Pm2. Further, both first and second parent *C. pepo* plants can comprise the mutant allele Pm2. Thus, any such methods using a *C. pepo* plant comprising the mutant allele Pm2 are part of this invention: selfing, backcrosses, hybrid production, crosses to populations, and the like.

DEPOSIT INFORMATION

A deposit of the Hollar Seeds proprietary pumpkin variety designated HSPMR7B1 containing mutant allele Pm2 of the present invention disclosed above and recited in the appended claims has been made with the American Type Culture Collection (ATCC), 10801 University Boulevard, Manassas, Va. 20110. The date of deposit was Aug. 6, 2010. The deposit of 2,500 seeds was taken from the same deposit maintained by Hollar Seeds since prior to the filing date of this application. All restrictions will be irrevocably removed upon granting of a patent, and the deposit is intended to meet all of the requirements of 37 C.F.R. §§1.801-1.809. The ATCC Accession Number is PTA-11250. The deposit will be maintained in the depository for a period of thirty years, or five years after the last request, or for the enforceable life of the patent, whichever is longer, and will be replaced as necessary during that period.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A *C. pepo* seed designated HSPMR7B1, wherein a representative sample of said seed was deposited under ATCC Accession No. PTA-11250.

2. A *C. pepo* plant, or a part thereof, produced by growing said *C. pepo* seed of claim 1.

3. A tissue culture of cells produced from the plant of claim 2, wherein said cells of the tissue culture are produced from a plant part selected from the group consisting of leaf, pollen, embryo, cotyledon, hypocotyl, meristematic cell, root, root tip, pistil, anther, flower, stem, fruit and petiole.

4. A protoplast produced from the plant of claim 2.

5. A protoplast produced from the tissue culture of claim 3.

6. A *C. pepo* plant regenerated from the tissue culture of claim 3, wherein said plant has all of the physiological and morphological characteristics of *C. pepo* plant HSPMR7B1.

7. A method for producing an $F_1$ hybrid *C. pepo* seed, wherein the method comprises crossing the plant of claim 2 with a different *C. pepo* plant and harvesting the resultant $F_1$ hybrid *C. pepo* seed.

8. A hybrid *C. pepo* seed produced by the method of claim 7.

9. A hybrid *C. pepo* plant, or a part thereof, produced by growing said hybrid seed of claim 8.

10. A method of producing an herbicide resistant *C. pepo* plant, wherein the method comprises transforming the *C. pepo* plant of claim 2 with a transgene, wherein the transgene confers resistance to an herbicide selected from the group consisting of imidazolinone, sulfonylurea, glyphosate, glufosinate, L-phosphinothricin, triazine and benzonitrile.

11. An herbicide resistant *C. pepo* plant produced by the method of claim 10.

12. A method of producing an insect resistant *C. pepo* plant, wherein the method comprises transforming the *C. pepo* plant of claim 2 with a transgene that confers insect resistance.

13. An insect resistant *C. pepo* plant produced by the method of claim 12.

14. The *C. pepo* plant of claim 13, wherein the transgene encodes a *Bacillus thuringiensis* endotoxin.

15. A method of producing a disease resistant *C. pepo* plant, wherein the method comprises transforming the *C. pepo* plant of claim 2 with a transgene that confers disease resistance.

16. A disease resistant *C. pepo* plant produced by the method of claim 15.

17. A method of producing a *C. pepo* plant with modified fatty acid metabolism or modified carbohydrate metabolism, wherein the method comprises transforming the *C. pepo* plant of claim 2 with a transgene encoding a protein selected from the group consisting of fructosyltransferase, levansucrase, α-amylase, invertase and starch branching enzyme or encoding an antisense of stearyl-ACP desaturase.

18. A *C. pepo* plant having modified fatty acid metabolism or modified carbohydrate metabolism produced by the method of claim 17.

* * * * *